United States Patent
Cicerone et al.

(10) Patent No.: US 7,101,693 B2
(45) Date of Patent: Sep. 5, 2006

(54) PLASTICIZED HYDROPHILIC GLASSES FOR IMPROVED STABILIZATION OF BIOLOGICAL AGENTS

(75) Inventors: Marcus T. Cicerone, Urbana, MD (US); Andrew Tellington, Sacramento, CA (US); Landon Trost, Lindon, UT (US); Alexei Sokolov, Fairlawn, OH (US)

(73) Assignee: Brigham Young University, Provo, UT (US)

( * ) Notice: Subject to any disclaimer, the term of this patent is extended or adjusted under 35 U.S.C. 154(b) by 25 days.

(21) Appl. No.: 10/199,061

(22) Filed: Jul. 22, 2002

(65) Prior Publication Data
US 2004/0014164 A1 Jan. 22, 2004

Related U.S. Application Data
(60) Provisional application No. 60/317,881, filed on Sep. 7, 2001.

(51) Int. Cl.
*C12N 9/96* (2006.01)
*A61K 31/04* (2006.01)

(52) U.S. Cl. .................. 435/188; 514/169; 514/180
(58) Field of Classification Search ................. 435/188; 514/169, 180
See application file for complete search history.

(56) References Cited

U.S. PATENT DOCUMENTS

| | | | |
|---|---|---|---|
| 3,761,420 A | 9/1973 | Bogardus | |
| 4,891,319 A | 1/1990 | Roser | |
| 5,149,653 A | 9/1992 | Roser | |
| 5,330,911 A | 7/1994 | Hubbell et al. | |
| 5,547,873 A | 8/1996 | Magneson et al. | |
| 5,565,318 A | 10/1996 | Walker et al. | |
| 5,851,984 A | 12/1998 | Matthews et al. | |
| 5,928,469 A | 7/1999 | Franks et al. | |
| 5,955,448 A | 9/1999 | Colaco et al. | |
| 5,972,395 A | 10/1999 | Saleeb et al. | |
| 6,028,066 A * | 2/2000 | Unger | 514/180 |
| 6,071,428 A | 6/2000 | Franks et al. | |
| 6,258,362 B1 | 7/2001 | Loudon et al. | |
| 6,290,991 B1 | 9/2001 | Roser et al. | |
| 6,426,210 B1 | 7/2002 | Franks et al. | |

FOREIGN PATENT DOCUMENTS

EP 0 270 799 B1 6/1988

OTHER PUBLICATIONS

R. Mouradian, C. Womerseley, L.M. Crowe, and J.H. Crowe, Biochem.. Biophys. Acta, 778 615 (1984).
J.F. Carpenter, L.M. Crowe, and J.H. Crowe, Biochimica et Biophysica Acta 923, 109 (1987).
Pikal, M.J., Rigsbee, D.R., The stability of insulin in crystalline and amorphous solids: observation of greater stability for the amorphous form. Pharm. Res. 14(10),1379–1387 (1997).
Izutsu, K.–I., Yoshioka, S., Terao, T., Effect of mannitol crystallinity on the stabilization of enzymes during freeze–drying. Pharm. Soc. Jap. 424(1), 5–8 (1994).
Tanaka, K, Takeda, T., Miyajima, K., Cryoprotective effect of saccharides on denaturation of catalase by freeze–drying, Chem. Pharm. Bull. 39(5), 1091–1094 (1991).
Costantino, H.R., Carrasquillo, K.G., Cordero, R.A., Mutenthaler, M., Hsu, C.C., Griebenwo, K, Effect of excipients on the stability and structure of lyophilized recombinant human growth, hormone, J. Pharm. Sci, 87,1412–1420 (1998).
Cleland JL, Lam X, Kendrick B, Yang J, Yang TH, Overcashier D, Brooks D, Hsu C,Carpenter JF, A specific molar ratio of stabilizer to protein is required for storage stability of a lyophilized monoclonal antibody. J Pharm Sci 90(3):310–21 (2001).
Carpenter, J.F., Crowe, L.M., and Crowe J.H., Stabilization of phosphofructokinase with sugars during freeze–drying: characterization of enhanced protection in the presence of divalent cations, Biochim. Biophys. Acta. 923, 109–115 (1987).
J.F. Carpenter, B. Martin, L.M. Crowe, and J.H. Crowe, Cryobiology 24, 445 (1987).
Mazzobre MF, Del Pilar Buera M., Combined effects of trehalose and cations on the thermal resistance of beta–galactosidase in freeze–dried systems. Biochim Biophys Acta 1473(2–3):337–44 (1999).
Chang BS, Kendrick BS, Carpenter JF., Surface–induced denaturation of proteins during freezing and its inhibition by surfactants. J Pharm Sci 85(12):1325–30 (1996).
J.F. Carpenter, B. Martin, SH. Loomis, and J.H. Crowe, Cryobiology 25, 327 (1988).

(Continued)

Primary Examiner—Ralph Gitomer
Assistant Examiner—Kailash C. Srivastava
(74) Attorney, Agent, or Firm—Buchanan Ingersoll, PC

(57) ABSTRACT

The stabilization of biomaterials such as proteins in a nominally dry, hydrophilic glassy matrix is vastly improved by the addition of an appropriate amount of a small-molecule pasticizer such as a glycol or DMSO to the formulation, while maintaining a glass transition temperature ($T_g$) that is above the storage temperature. By plasticizing the glasses, their ability to preserve proteins is improved by as much as 100 times over the unplasticized glass at room temperature. The plasticizer confers the greatest beneficial effect when it is dynamically coupled into the bulk glass, and this coupling occurs over a fairly narrow range of plasticizer concentration. Methods are described in which a small-molecule plasticizer can be incorporated into a glass made of much larger molecules (e.g. a polymeric glass), with desired dynamic coupling, via a molecule that is believed to act as a dynamic linker. Protein preservation data was obtained from two enzymes, horseradish peroxidase (HRP) and alcohol dehydrogenase (ADH).

26 Claims, 9 Drawing Sheets

OTHER PUBLICATIONS

Hinrichs WL, Prinsen MG, Frijlink HW, Inulin glasses for the stabilization of therapeutic protein Hinrichs WL, Prinsen MG, Frijlink HW.Int J Pharm 215(1–2):163–74 (2001).

Sun, W.Q. and P. Davidson, Effect of dextran molecular weight on protein stabilization during freeze–drying and storage, CryoLett. 22, 285–292 (2001).

Anchordoquy TJ, Izutsu KI, Randolph TW, Carpenter JF, Maintenance of quaternary structure in the frozen state stabilizes lactate dehydrogenase during freeze–drying. Arch. Biochem. Biophys. 390(1), 35–41 (2001).

Yoshioka S, Aso Y, Kojima S, Tanimoto T., Effect of polymer excipients on the enzyme activity of lyophilized bilirubin oxidase and beta–galactosidase formulations. Chem Pharm Bull (Tokyo) 48(2):283–5 (2000).

Mattern M, Winter G, Kohnert U, Lee G., Formulation of proteins in vacuum–dried glasses. II. Process and storage stability in sugar–free amino acid systems. Pharm Dev Technol 4(2):199–208 (1999).

Allison SD, Manning MC, Randolph TW, Middleton K, Davis A, Carpenter JF., Optimization of storage stability of lyophilized actin using combinations of disaccharides and dextran. J Pharm Sci 89(2):199–214 (2000).

Kreilgaard L, Frokjaer S, Flink JM, Randolph TW, Carpenter JF. Effects of additives on the stability of recombinant human factor XII during freeze–drying and storage in the dried solid. Arch Biochem Biophys 360(1):121–34 (1998).

Izutsu K, Yoshioka S, Kojima S., Increased stabilizing effects of amphiphilic excipients on freeze–drying of lactate dehydrogenase (LDH) by dispersion into sugar matrices. Pharm Res 12(6):838–43 (1995).

Kim AI, Akers MJ, Nail SL.The physical state of mannitol after freeze–drying: effects of mannitol concentration, freezing rate, and a noncrystallizing cosolute. J Pharm Sci 87(8):931–5 (1998).

Lueckel B, Bodmer D, Helk B, Leuenberger H., Formulations of sugars with amino acids or mannitol—influence of concentration ratio on the properties of the freeze–concentrate and the lyophilizate. Pharm Dev Technol 3(3):325–36 (1998).

Kasraian K, Spitznagel TM, Juneau JA, Yim K., Characterization of the sucrose/glycine/water system by differential Scanning calorimetry and freeze–drying microscopy. Pharm Dev Technol 3(2):233–9 (1998).

Heller MC, Carpenter JF, Randolph TW., Protein formulation and lyophilization cycle design: prevention of damage due to freeze–concentration induced phase separation. Biotechnol Bioeng 63(2):166–74 (1999).

Lueckel B, Helk B, Bodmer D, Leuenberger H. Effects of formulation and process variables on the aggregation of freeze–dried interleukin–6 (IL–6) after lyophilization and on storage. Pharm. Dev. Technol. 3(3):337–46 (1998).

Conrad PB, Miller DP, Cielenski PR, de Pablo JJ., Stabilization and preservation of Lactobacillus acidophilus in saccharide matrices. Cryobiology 41(1):17–24 2000.

Miller, D.P., Andreson, R.E., and de Pablo, J.J., Stabilization of lactate dehydrogenase following freeze–thawing and vacuum–drying in the presence of trehalose and borate, Pharm. Res. 15 (8), 1215–1221 (1998).

Her, L.M., Deras, M., Nail, S.M., Electrolyte–induced changes in glass transition temperatures of freeze–concentrated solutes, Pharm. Res. 12 (5), 768–772 (1995).

Miller, D.P, de Pablo, J.J., Corti, H.R, Viscosity and glass transition temperature of aqueous mixtures of trehalose with borax and sodium chloride, J. Phys. Chem. B. 103, 10243–10249 (1999).

Kasraian K, DeLuca PP.The effect of tertiary butyl alcohol on the resistance of the dry product layer during primary drying. Pharm Res 12(4):491–5 (1995).

Carpenter, J.F., Pikal, M.J., Chang, B.S., Randolph, T.W., Rational design of stable lyophilized protein formulations: some practical advice. Pharm. Res. 14(8), 969–975 (1997).

Bell, L.N., Haeman, M.J., and Muraoka, L.M., Thermally induced denaturation of lyophilized bovine somatotropin and lysozyme as impacted by moisture and excipients, J. Pharm. Sci, 84 (6), 707–712 (1995).

Buitink, J., Dries, I. J. van den, Hoekstra, F.A, Alberda, M., and Hemminga, M.A., High Critical Temperature above $T_g$ May Contribute to the Stability of Biological Systems, Biophys. vol. 79(2), 1119–1128 (2000).

S.P. Duddu, and P.R. Dal Monte, Pharm. Research, 14, 591 (1997).

Wang, W., Lyophilization and development of solid protein pharmaceuticals, Int. J. Pharm. 203, 1–60 (2000).

Tan, C.S., van Ingen, C.W., Talsma, H., van Miltenburg, J.C., Setffensen, C.L., Vlug, Ij. A., and Stalpers, J.A., Freeze–drying of fungi: influence of composition and glass transition temperature of the protectant, Cryobiology 32, 60–67 (1995).

Uritani, M., Tanai, M., Yoshinaga, K, Protective effect of disacchairdes on restriction endonuclease during drying under vacuum. J. Bioichem 117, 774–779 (1995).

Buera, M.P., Rossi, S., Moreno, S., Chirife, J., Stabilization of restriction enzyme EcoRi dried with trehalose and other selected glass–forming solutes, Biotechnol. Prog. 13, 609–616 (1997).

Rariy, R.V., Klibanov, A.M., Correct protein folding in glycerol, Proc. Natl. Acad. Sci, USA 94, 13520–13523 (1997).

Carpenter, J.F., Crowe, J.H, Modes of stabilization of a protein by organic solutes during dessication, Cryobiology 25, 459–470 (1988).

Buera, M.P., Rossi, S., Moreno, S., Chirife, J., DSC confirmation that vitrification is not necessary for stabilization of the restriction enzyme ecoRI dried with saccharides, Biotechnol. Prog. 15, 577–579 (1999).

Gekko, K., Timasheff, S.N., Mechanism of protein stabilization by glycerol: preferential hydration in glycerol–water mixtures, Biochemistry 20, 4667–4676 (1981).

T. Inoune M.T. Cicerone, and M.D. Ediger, Macromolecules 28, 3425 (1995).

M. Vogel, P. Medick, E. Rossler, J. Mol. Liquids 86, 103 (2000).

K.C. Fox, Putting proteins under glass, Science 267, 1992 (1995).

Shamblin, S.L., Tang, X., Chang, L., Hancock, B.C., and Pikal, M.J., Characterization of the time scales of molecular motion in pharmaceutically important glasses. J. Phys. Chem. B 103, 4113–4121 (1999).

Mazzobre, M.F., Buera, M.P., Chirife, H., Glass transition and thermal stability of lactase in low–moisture amorphous polymeric matrices. Biotechnol. Prog. 13, 195–199 (1997).

Yoshioka, S., Aso, Y., Izutsu, K.–I., Terao, T., Application of accelerated testing for shelf–life prediction of commercial protein preparations. J. Pharm. Sci. 83, 454–456 (1994).

Sun, W.Q., Davidson, P., Chan, H.S.O., Protein stability in the amorphous carbohydrate matrix: relevance to anhydrobiosis. Biochim. Biophys. Acta. 1425, 245–254 (1998).

Encinas, MV, Gonzalez–Nilo FD, Andreu JM, Alfonso C, Cardemil E. urea–induced unfolding studies of tree– an dligan–bound tetrameric ATP–dependent *saccharomyces cerevisiae* phosphoenolupyruvate carbohykinase. Influence of quaternary structure on protein conformational stability. Int. J. Biochem. Cell Biol. 34(6): 645–56 (2002).

Gebicka, L., and Gabicki, J.L., Dimethyl sulfoxide rather than superoxide is the reactive species in horseradish peroxidase–$KO_2$/dimethyl sufloxide system, Biochem. Mol. Bio. Int. 37(5) 1021–1026 (1995).

Myers, J.S., Jakoby, W.B., Glycerol as an agent eliciting small conformaitional changes in alcohol dehydrogenase. J. Biol. Chem. 250 (10), 3785–3789 (1975).

Duran, N., Baeza, J., Freer, F., Brunet, J.E., Gonzalez, F.A., Sotomayor, C.P., Faljoni–Alario, A., Dimethyl sulfoxide as a chemical and biological probe: conformational effect on peroxidase systems, Biochem. And Biophys. Res. Comm., 103(1), 131–138 (1981).

Yoshioka et al, "The Effect of Excipients on the Molecular Mobility of Lyophilized Formulation, as Measured by Glass Transition Temperature and NMR Relaxation–Based Critical Mobility Temperature", Pharmaceutical Research, vol. 16, No. 1, 1999, pp. 135–140.

Yoshioka et al, "Molecular Mobility of Protein in Lyophilized Formulations Linked to the Molecular Mobility of Polymer Excipients, as Determined by High Resolution $^{13}C$ Solid–State NMR"; Pharmaceutical Research, vol. 16, No. 10, 1999, pp. 1621–1625).

Schebor et al, "Glass Transition Temperatures and Fermentative Activity of Heat–Treated Commercial Active Dry Yeasts"; Biotechnol. Prog. 2000, vol. 16, pp. 163–168.

Sathish et al, "Influence of metal ions on structure and catalytic activity of papain"; Indian Journal of Biochemistry & Biophysics, vol. 37, Feb. 2000, pp. 18–27.

Xie et al, "The thermodynamic mechanism of protein stabilization by trehalose"; Biophysical Chemistry, vol. 64, 1997, pp. 25–43.

Wang, "Instability, stabilization, and formulation of liquid protein pharmaceuticals"; International Journal of Pharmaceutics, vol. 185, 1999, pp. 129–188.

Rossi et al, "Stabilization of the Restriction Enzyme *EcoRI* Dried with Trehalose and Other Selected Glass–Forming Solutes"; Biotechnol. Prog. 1997, vol. 13, pp. 609–616.

Marcolongo et al, "Bioactive glass fiber/polymeric composites bond to bone tissue"; Nov. 1996, pp. 161–170.

Chang et al, "Physical Factors Affecting the Storage Stability of Freeze–Dried Interleukin–1 Receptor Antagonist: Glass Transition and Protein Conformation"; Archives of Biochemistry and Biophysics; vol. 331, No. 2, Jul. 15, 1996, Article No. 0305, pp. 249–258.

Carpenter et al, "Cryoprotection of Phosphofructokinase with Organic Solutes: Characterization of Enhanced Protection in the Presence of Divalent Cations"; Archives of Biochemistry and Biophysics, vol. 250, No. 2, Nov. 1, 1986, pp. 505–512.

Bell, "Peptide Stability in Solids and Solutions"; Topical Paper, Biotechnol. Prog. 1997, vol. 13, pp. 342–346.

Andersson et al, "Stabilizing effect of chemical additives against oxidation of lactate dehydrogenase"; Biotechnol. Appl. Biochem. vol. 32, 2000, pp. 145–153.

Davidson et al, "Effect of Sucrose/Raffinose Mass Ratios on the Stability of Co–Lyophilized Protein During Storage Above $T_g$", Pharmaceutical Research, vol. 18, No. 4, 2001, pp. 474–479.

Chang et al, "Development of a Stable Freeze–dried Formulation of Recombinant Human Interleukin–1 Receptor Antagonist"; *Pharmaceutical Research*, vol. 13, No. 2; pp. 243–249; 1996.

Lourdin et al, "Antiplasticization" in Starch–Glycerol Films?; *Institut National de la Recherche Agronomique*; pp. 1047–1053; received Feb. 6, 1996; accepted Apr. 16, 1996.

Gaudin et al, "Antiplasticisation and oxygen permeability of starch–sorbitol films"; *Carbohydrate Polymers*, (43) (2000); pp. 33–37; accepted Dec. 13, 1999.

Lourdin et al, "Study of plasticizer–oligomer and plasticizer–polymer interactions by dielectric analysis: maltose–glycerol and amylose–glycerol–water"; *Carbohydrate Research*, 306 (1998), pp. 551–558, received Jun. 9, 1997, accepted in revised form Dec. 26, 1997;

Noel et al, "A comparative study of the dielectric relaxation behaviour of glucose, maltose, and their mixture with water in the liquid and glassy states"; *Carbohydrate Research*, 282 (1996); pp. 193–206, received Jun. 13, 1995, accepted Nov. 14, 1995.

\* cited by examiner

Enzyme activity as a function of time at 37 °C for enzyme in two different stabilizing glasses (◆) dextran glass; (▲) trehalose glass.

Enzyme deactivation times plotted in Arrhenius format. (◆) trehalose; (■) mixture of dextran, inulin, and glycerol; (▲) mixture of dextran and glycerol. All data are linear, with linear fit $R^2$ values of 0.997, 0.989, and 0.9998 respectively.

FIG. 3

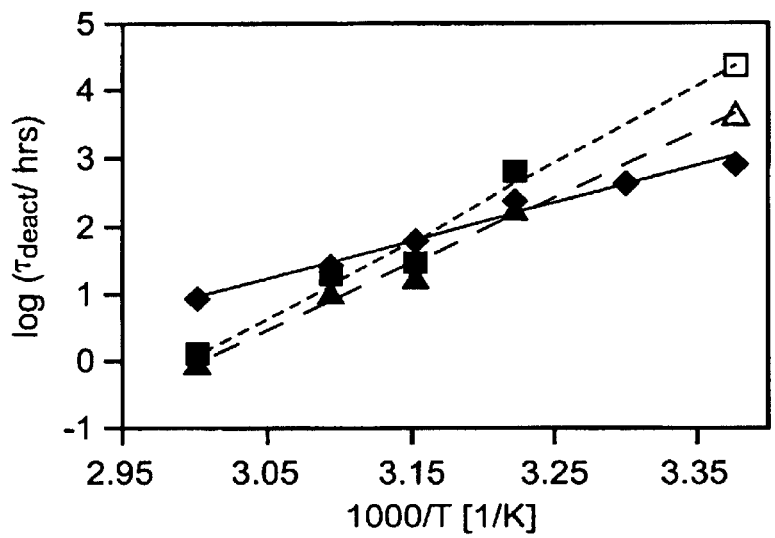

Protective effect for HRP of trehalose glasses plasticized with DMSO or glycerol. (♦) trehalose; (■) trehalose with 10% dimethyl sulfoxide; (▲) trehalose with 5wt% glycerol. Open symbols represent extrapolated values of stability lifetimes.

FIG. 4

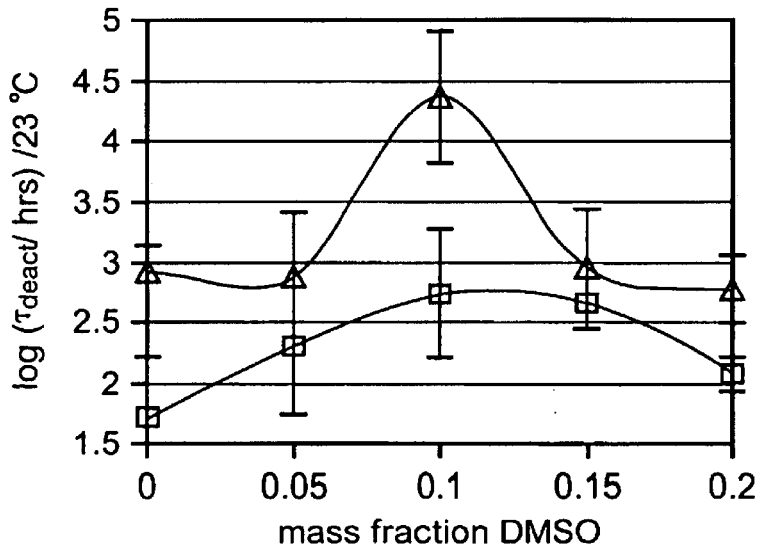

HRP deactivation times extrapolated to room temperature for bioprotective glasses plasticized with varying amounts of DMSO; (△) trehalose, (□) maltitol.

HRP deactivation times extrapolated to room temperature for bioprotective glasses plasticized with varying amounts of glycerol; (◇) raffinose (△) trehalose, (□) lactose, (○) maltitol.

Temperature dependence of HRP deactivation time for (▲) dextran and (◆) 90% dextran, 10% glycerol.

Protective properties of plasticized polymeric glasses.
(♦) dextran; (■) dextran with 10wt% glycerol;
(●) dextran with 10wt% inulin; (▲) dextran with 10wt% inulin and 10wt% glycerol. Open symbols represent extrapolated values of stability lifetimes.

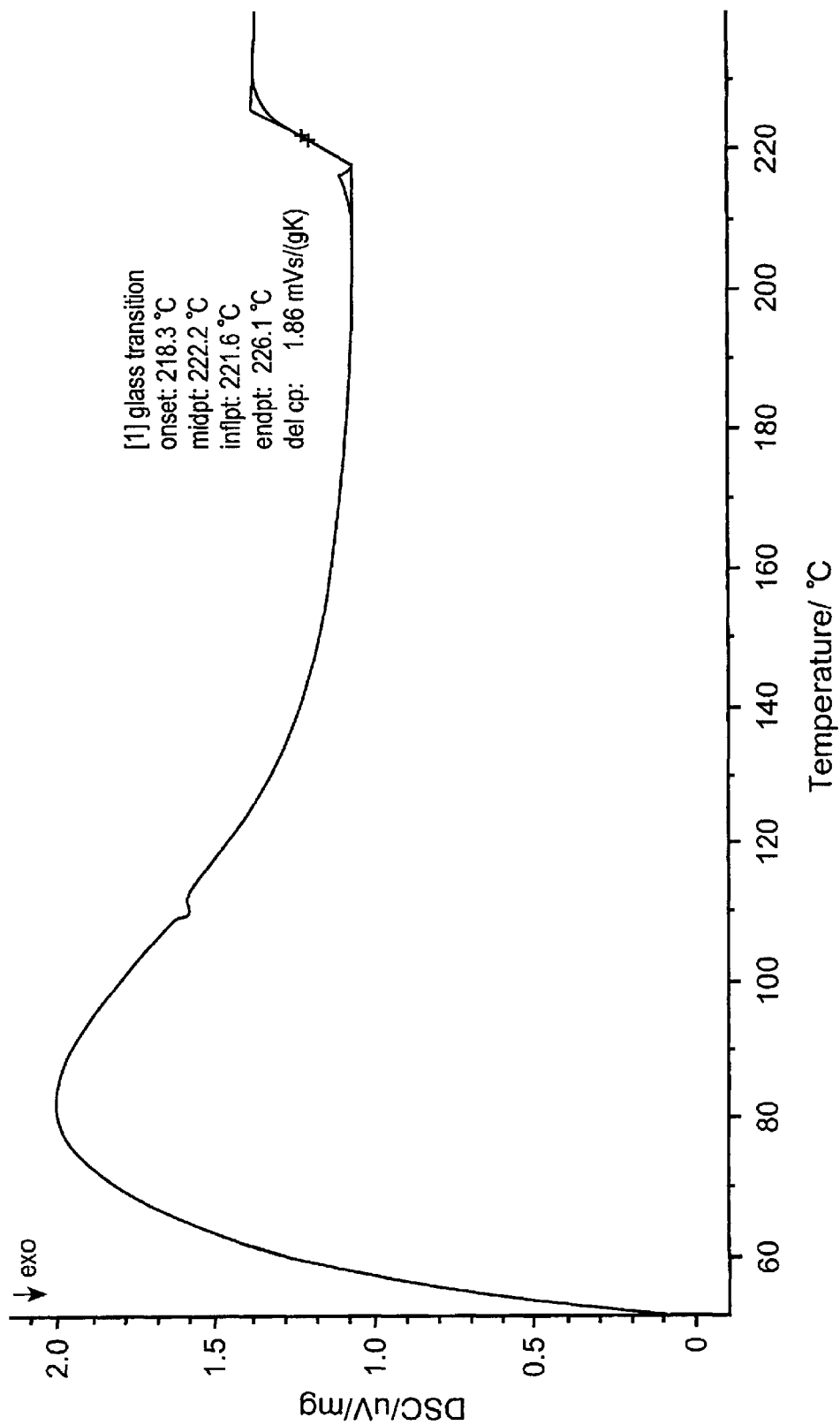

FIG. 9

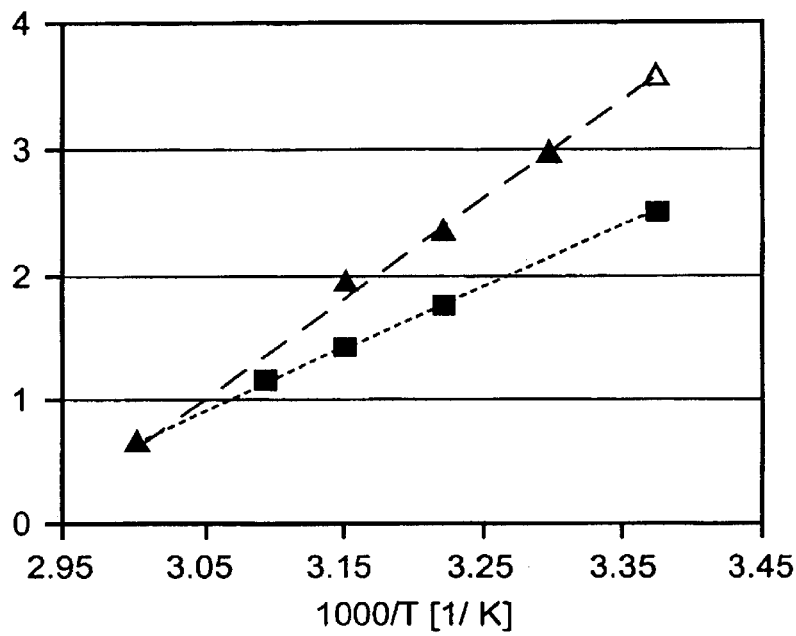

Effect of intermediate-sized linkers on plasticized polymeric glass. (▲) dextran with 15wt% each of maltitol and glycerol; (■) dextran with 10wt% of glycerol. Open symbol represents extrapolated value of stability lifetimes.

FIG. 10

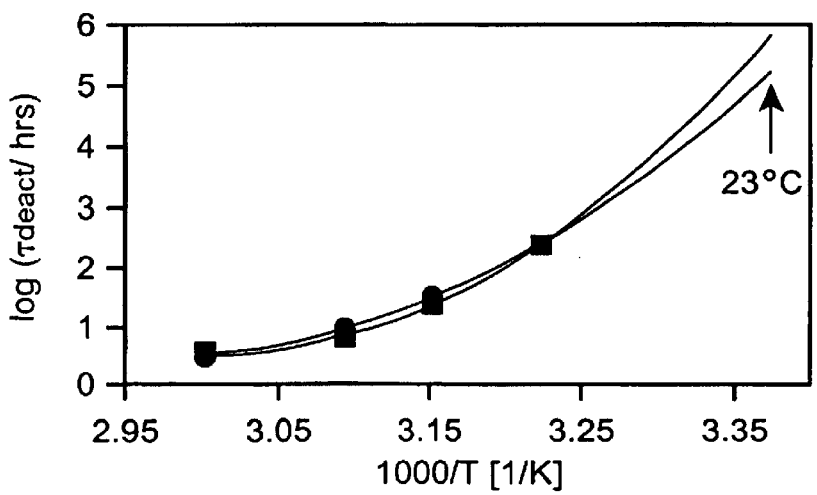

Two of the systems we have tested appear to exhibit non-Arrhenius behavior. (■) ficoll with 10 wt% each of inulin and glycerol; (●) dextran with 10 wt% each of maltitol and ethylene glycol.

PLASTICIZED HYDROPHILIC GLASSES FOR IMPROVED STABILIZATION OF BIOLOGICAL AGENTS

CROSS-REFERENCE TO RELATED APPLICATIONS

This application claims the benefit of U.S. Provisional Application No. 60/317,881, filed Sep. 7, 2001, the disclosure of which is incorporated herein in its entirety.

BACKGROUND OF THE INVENTION

1. Field of the Invention

This invention relates generally to the stabilization/preservation of biological agents in glassy matrices and more particularly to the use of plasticizers to improve the stability of proteins in hydrophilic glasses.

2. Description of the Related Art

Recent advances in the field of biotechnology have led to the production of formulations containing proteins such as enzymes, peptides and many other biological agents suitable for use as pharmaceuticals, veterinarian preparations and foods. Many of these formulations are in the form of aqueous preparations which are unstable and must be dried to preserve the efficacy of the biological agent. A protective agent is frequently required to prevent any deleterious effects as a result of the drying procedure.

It has long been known that proteins and other biological structures can be stored in a dry state while retaining some or all of their functionality. Some plants and simple animals can survive in a dry, dormant state for extended periods of time, and function normally when rehydrated. Well over a decade ago, it became clear that carbohydrate glass plays a central role in anhydrous preservation of biological agents in nature,[1,2] but there is still a significant amount of uncertainty as to the exact mechanisms that are important in biopreservation.

There are probably two major classes of stabilization mechanisms. One class, kinetic stabilization, is brought about by the slow dynamics in a glass. The glass is thought to have the ability to "form fit" the protein, and impart to some degree its dynamics on the protein, and to retard the diffusion of potentially harmful, external species. There is circumstantial evidence for this mechanism, inasmuch as the crystalline phase of a material will not provide stabilization to proteins, while the glassy form of the same material will provide good stabilization.[3,4] The other major mechanistic class, thermodynamic stabilization, is often viewed as being mediated through the ability of the carbohydrate to "replace" water at the protein surface. Tanaka et al.[5] showed that catalase denaturation upon freeze-drying was minimized when there was at least enough glass-former to occupy the hydrophilic sites on the protein. Cleland et al.[6] reported supporting results for minimization of soluble aggregation formation of rhGH (recombinant human growth hormone) in lyophilized form. Carpenter et al.[7] performed similar experiments on a monoclonal antibody, and found that in order to maximally stabilize the antibody against several stress modes, a mole ratio of lyoprotectant to protein was needed that was twice that reported as required to protect against aggregation or denaturation on drying. Other components in the formulation, such as ionic species[8,9,10] and surfactants may also contribute to the thermodynamic stabilization of the protein in the glass.

Typical materials for the formulation of lyoprotective glasses have been generally limited to single sugars and sugar alcohols,[12,13,14,15] polymeric sugars such as inulin,[16] ficoll and dextran,[17,18] synthetic polymers such as dextran DEA, dextran sulfate, polyethylene glycol, polyvinyl pyrrolidone, polyacrylamide, or polyethyleneimine,[19,20] and some amino acids.[21] Materials such as those mentioned above are referred to as "standard" glassforming materials because they are in more-or-less common use.

Various mixtures of the standard glassforming materials have also been used in formulations for stabilization of proteins, such as polymers and small carbohydrates.[22,23,24,25] These mixtures can yield materials with desirable physical characteristics, such as increased mechanical toughness, increased glass transition temperature ($T_g$), or decreased probability of crystallization. The desirability of these characteristics is often related to ease of processing, but some of these mixtures are also reported to yield increased lifetime of stabilized protein in the glass.[23,24] Amino acids or crystallizing alcohols used as additives in carbohydrate glasses comprise another class of mixtures of standard materials. Additives in this class have very high melting temperatures ($T_m$>100° C.), and typically have $T_g$ values within 20° C. to 30° C. of room temperature. The wide temperature range between $T_m$ and $T_g$ makes these materials poor glassformers, and predisposes them to crystallization rather than glass-formation. While they are known to be mild plasticizers to the glass,[26,27] they are typically used because of their propensity to crystallize. These compounds are often induced to crystallize during the freezing step, thus they become a support against structural collapse during drying.[28] Upon crystallization they may also form microchambers, inhibiting phase separation.[29] While they do impart desirable physical characteristics to the formulation, the presence of crystalline mannitol or glycine in an otherwise glassy formulation has been shown to be destabilizing to several proteins.[30,4]

One recent and important improvement to the standard-materials-only approach is the addition of borate ion.[31] The action of borate ion is very different than the action of salts typically added to glassy biopreservation formulations. Borate is known to function as a cross-linking agent for OH groups (e.g. on the sugars), and its addition to a carbohydrate glass increases the $T_g$ of the mixture by as much as 80° C.[32] Thus, it acts as a powerful anti-plasticizing agent, whereas the presence of monovalent[33,34] and divalent cations[10] does not significantly alter $T_g$ of the glass by comparison.

It is important to note that essentially all of the "standard" glassforming materials in use for preserving biological agents in a dry state have glass transitions above or near room temperature. We are aware of two exceptions: surfactants, which are employed as a protection against unfolding during freezing,[11] and t-butyl alcohol (TBA), which was used in freeze-drying as a facilitating agent for sublimation of ice crystals.[35] The authors of that report indicated that the presence of TBA did not change the collapse temperature of the freeze-dried cake. Thus, the TBA did not act as a plasticizer, probably because it sublimed off with the water. Other than these exceptions, materials with $T_g$ far below room temperature are not typically used to enhance the biopreserving efficacy of a lyoprotective glass. This is not surprising, as these materials will typically be strong plasticizers of the glass (reduce its $T_g$), and this is typically viewed as undesirable.[36] It is sometimes observed[37] and commonly asserted[38,39] that a higher host $T_g$ will lead to better preservation of biological agents at a given storage temperature. One might conclude from such observations and assertions that plasticization is always deleterious to the bio-stabilizing capacity, and in fact, statements have been made in the literature with that underlying assumption.[40]

Small-molecule hydrophilic solutes such as glycerol, propylene glycol, and dimethyl sulfoxide (DMSO) are commonly used to stabilize proteins in solution against cryogenic stress. However, being liquids at room temperature, and possessing $T_g$ values far below room temperature, they are strong plasticizers, and for the reasons mentioned above are typically avoided in lyoprotective glass formulations. There is one study where they have been evaluated in glasses for preservation of fungus spores. In the study, addition of ~8 wt % glycerol or DMSO to the glass formulation was tested for fungus preservation.[41] The authors in this study observed a negative effect on the fungus spore stability caused by plasticizers.

There are two studies wherein glycerol was present in the biopreservation formulation somewhere in the range of 20 wt % to 22 wt %, and originated from the solution in which the enzyme was supplied.[42,43] In both of these cases, the formulation tested was not glassy. One of these reports included reasonable levels of protein stabilization, although those results were not quantitative.[43] Several studies have shown that proteins can be stabilized to some extent in the presence of glycerol alone, or solutions of glycerol, at temperatures well above the glass transition temperature of the solution.[44,45,46] This is thought to occur by an indirect mechanism that involves hydration water.[47]

In a series of similar single-component glasses, the glasses with lower $T_g$ will have slower dynamics at $T_g$.[48] This effect is due, at least in part, to a reduced upper length scale of motions that are relevant to the glassy dynamics. In spite of cautions to the contrary in the literature, the present inventors reasoned that the addition of a plasticizer might slow the dynamics within the glass, and improve stability of preserved proteins, provided that the small molecule is dynamically linked to the larger glass-forming molecule. This proviso is non-trivial, as individual components in mixtures of materials with widely differing $T_g$ values are known to exhibit uncoupled dynamics.[49]

Despite the progress which has been made in understanding the underlying mechanisms of protective agents such as glassy matrices in freeze-drying of biological agents such as enzymes, there remains a need to develop methods and compositions which improve the long-term stability of dried biological agents.

SUMMARY OF THE INVENTION

This invention is based on the discovery that a class of low molecular weight compounds function as plasticizing agents for "non-cryogenic" lyoprotective glasses and extend the stabilization of biological agents such as enzymes far beyond that expected by those skilled in the art. Here, "non-cryogenic" glasses refer to those glasses designed for storage near or above 0° C. (i.e., not under frozen conditions), and especially those designed for storage at room temperature and above.

The present invention represents an approach to formulating bio-protective glasses that is fundamentally different than used heretofore. Small-molecule liquids which are at least partially hydrophilic, are used as additives in glass-forming formulations for stabilization of bioagents such as proteins which contain otherwise "standard" components. Examples of these plasticizers include, but are not limited to, dimethyl sulfoxide (DMSO), glycerol, propylene glycol, and ethylene glycol. These materials are all "non-crystalline," i.e., they are not expected to crystallize in situ. Furthermore, they all have $T_g$ values below 0° C., and thus, are powerful plasticizers to the glass. These characteristics serve to define "plasticizing agents" as that term is used herein. These plasticizers are differentiated from plasticizers such as manitol and amino acids, etc., both by their lower $T_g$ values and by the fact that they do not have a propensity to crystallize in the final product.

Surfactants are commonly used in bioprotective glasses, at concentrations near the critical micelle concentration[36] (CMC), as agents to protect against protein aggregation. They also function as plasticizing agents as defined above, however; they are excluded from the present invention as long as they are used at concentrations near the CMC. The CMC is typically less than 10 mM for surfactants. At these low concentrations they are effective in preventing freezing-induced aggregation,[36] but they do not significantly plasticize the glass (i.e., they do not change $T_g$ of the glass by more than 1–2° C.).

The intentional incorporation of plasticizers into glasses for lyophilization is commonly cautioned against.[36,40] Glycerol, DMSO, and polyethylene-glycol have been evaluated as plasticizing agents for glasses prepared for preservation of fungus spores, but to reported negative effect,[41] and in non-glassy formulations with no noted improvements over the unplasticized glass.[42,43] In these previous studies, 20–22 wt % glycerol was used, and, based on the present inventors' experience with glycerol-plasticized glasses, no improvement would be expected in room-temperature stabilization of biological materials at this high level of glycerol.

The incorporation of plasticizing agents into glasses, in the appropriate concentration range, can produce an "improved" glass, where "improved" denotes a greater bioprotective capability of the plasticized glass than that of the unplasticized glass. The range over which this improvement is usually seen is on the order of about 3 wt % to about 15 wt %, but may be outside this range for other combinations of materials. As will become clear below, the particular optimal amount of plasticizer will depend on the intended storage temperature. The upper limit of the plasticizer concentration will be that concentration at which the formulation is no longer glassy at the storage temperature.

The plasticizing agents are believed to act by reducing the lengthscale on which dynamics are hindered in the glass, and also by slowing the dynamics of the glass. Evidence suggests that the beneficial effect of these plasticizers is realized when the plasticizer dynamics are coupled with the bulk glassformer. This coupling can be accomplished via a "dynamic linker" when the timescales of dynamics of the individual components are separated sufficiently to require it, as in the case of plasticized polymeric glasses.

By virtue of the present discovery, glasses with bioprotective capability equal to or better than the best single-component glasses can be made using materials that are significantly less expensive than single-component glasses. In one example shown below, an extrapolated enzyme activity lifetime of 10 years at room temperature (HRP in a dextran, maltitol, DMSO glass) is obtained whereas currently an enzyme activity lifetime of 18 months is considered an achievement.[50]

BRIEF DESCRIPTION OF THE DRAWINGS

FIG. 3 shows protective effect for HRP of trehalose glasses plasticized with DMSO or glycerol.

FIG. 4 shows HRP deactivation times extrapolated to room temperature for bioprotective glasses plasticized with varying amounts of DMSO.

FIG. 8(a) shows a thermogram of dextran glass.

FIG. 9 shows the effect of intermediate-sized linkers on plasticized polymeric glass.

FIG. 10 shows two of the systems tested which appear to exhibit non-Arrhenius behavior.

DETAILED DESCRIPTION OF PREFERRED EMBODIMENTS OF THE INVENTION

Figure 1:
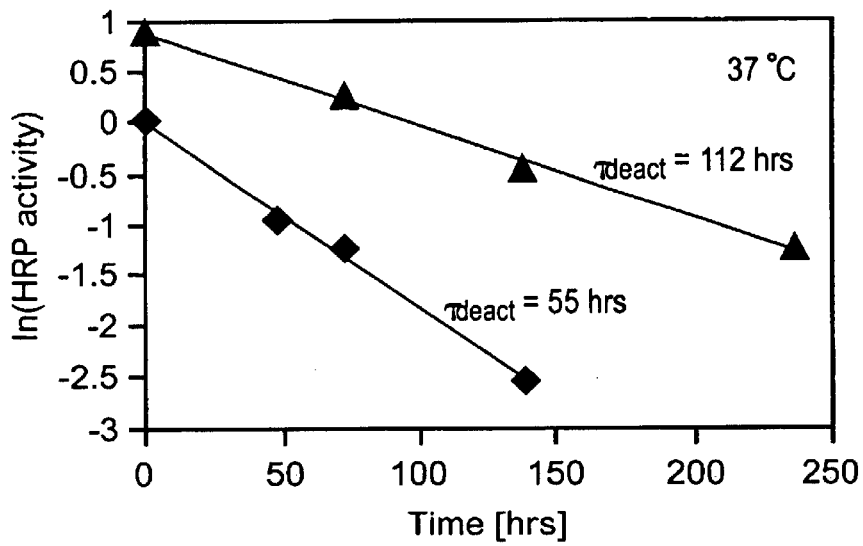
FIG. 1 shows enzyme activity as a function of time at 37° C. for enzyme in two different stabilizing glasses.

Described hereinafter are the detailed results of research into improved formulations for bioprotective glasses. A suitable method is described for sample preparation, although it should be understood that other known techniques can be employed to prepare the formulations of the invention. While freeze-drying was used to make the samples, other techniques such as spray-drying and vacuum-drying, can be used. The materials used in the following examples are for illustrative purposes only. The examples are intended to be merely exemplary and in no way limiting.

Materials

All enzymes, reagents, glassforming materials, and plasticizers were obtained from Sigma, except for poly-vinyl alcohol (PVA), which was obtained from Spectrum. All materials were used as received. Unless specified otherwise, dextran refers to 70 k MW dextran, ficoll refers to 70 k MW ficoll, PVP refers to K 29–32 polyvinylpyrrolidone, and PVA refers to poly-vinyl alcohol (24–32 cps @ 4% in $H_2O$, and 20° C.). The peroxidase (HRP), was type II from horseradish, and the alcohol dehydrogenase (ADH) was from bakers yeast. The bovine serum albumin (BSA) was fraction V.

Sample Preparation

All samples were prepared in aqueous solution to contain 100 mM $CaCl_2$, and 300 µg/ml Tween 20, 0.5 wt % BSA, and 60 nM enzyme for stabilization (HRP or ADH). All solutions contained 20 wt % glass-former and plasticizer (except PVP and PVA solutions, which were 13 wt % and 8 wt % respectively). $CaCl_2$ and Tween 20 were first added to stock solutions of glass-former. After these were mixed well, the BSA and enzyme to be stabilized were added. HRP solutions were made up in 50 mM histidine buffer (pH6.0), and ADH solutions were made up in 50 mM Tris buffer (pH 7.0). All solutions were made with milliQ water.

In preparation for freeze-drying, each sample was divided into aliquots of approximately 150 µl. The aliquots were dispensed into 1.7 ml Eppindorf microfuge tubes, and these were then placed, uncapped into the freeze-dryer for lyophilization.

A typical freeze-drying protocol is given in Table I below:

TABLE I

| Temperature | Duration | Pressure |
| --- | --- | --- |
| −40° C. | ~1 hr. (or until frozen) | 760 torr |
| −20° C. | ~6 hrs. (or until primary drying is done) | 30 mtorr |
| −8° C. | ~3 hrs. | 30 mtorr |
| 25° C. | ~24 hrs.* | 30 mtorr |

*Final drying is probably complete before the 24 hr. Figure included here.

After the final drying step, the glassy samples were removed from the freeze-dryer and immediately capped to prevent excessive re-absorption of moisture from the ambient air. It was determined that there was typically <0.1% residual water, and dried masses were consistent with plasticizer not being lost during the freeze-drying. This is noteworthy, as some of the plasticizers, such as DMSO would, in the pure state, be lost to evaporation during the last stage of the freeze-drying protocol (24 hours at 25° C. and 30 mtorr). The fact that the plasticizer is not lost indicates that it interacts strongly with the glassy matrix.

Enzymatic Assay

Assays of enzyme activity were carried out in 96-well plates on a Ceres UV900HDI plate reader. Enzymatic activity of both HRP and ADH was assayed by colorometric methods. Details are given below.

HRP catalyzes the following dimerization reaction when in the presence of an appropriate substrate, such as hydrogen peroxide

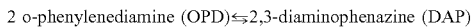
2 o-phenylenediamine (OPD)⇌2,3-diaminophenazine (DAP)

Absorbance of the solution at 450 nm is approximately proportional to [DAP]. 25 µl of HRP solution (rehydrated from the freeze-dried state) was added to 240 µl of a solution containing 8.3 mM $H_2O_2$, 1.3 mM OPD, and 50 MM histidine (pH 6.0) in each well of the plate. The initial rate of change in optical density at 450 nm was measured and the HRP activity obtained from this value via a calibration curve.

ADH catalyzes the following reaction:

ethanol+NAD⇌$CH_3CHO$+$NADH^-$+$H^+$

Absorbance of the solution at 340 nm is approximately proportional to [$NADH^-$]. 100 µl of ADH solution (rehydrated from the freeze-dried state) was added to 150 µl of a solution containing 1.7 mM NAD, 387 nM ethanol, and 50 mM Tris (pH 7.0) in each well of the plate. The initial rate of change in optical density at 340 nm, was measured and the ADH activity obtained from this value via a calibration curve.

Calibration curves are established with standard solutions of enzyme, obtained by serial dilutions of a known concentration of fresh enzyme. HRP concentrations for calibration curves ranged from 10 nM to 10 pM, and those for ADH calibration ranged from 25 nM to 2.5 pM. The nominal enzyme concentration of the rehydrated, stabilized enzyme aliquots is 7.6 nM in all cases, giving three orders of magnitude over which one could measure enzyme activity. In all assays, initial rates of change of optical density are established by acquiring data for 7 minutes, with readings at 5 s intervals.

Evaluation of Formulations

The effectiveness of a particular enzyme-stabilizing formulation was evaluated by measuring enzyme activity after separate, sealed aliquots of the stabilized enzyme have been placed at a controlled temperature for a series of time periods. Heat-stressed and frozen (control) aliquots were rehydrated in buffer and tested in adjacent rows on a 96 well plate for residual enzyme activity as described above. It was observed that enzyme activity (both HRP and ADH) showed an initial exponential decrease with time under heat-stress. FIG. 1 shows an example of measured enzyme activity decrease as a function of time; the time dependence of the natural log of HRP activity is plotted for two different glasses at 37° C. Values of $\tau_{deact}$ were typically determined from one frozen control (unstressed) aliquot, and three heat stressed aliquots, as in FIG. 1. The fact that the data fall on a straight line in this plot indicates exponential activity decay, and a lifetime for enzyme activity decay ($\tau_{deact}$) is calculated as $\tau_{deact}=-1/m$, where in is the slope of the linear best fit to $\ln(\tau_{deact})$ vs. time data, e.g. the solid lines in FIG. 1.

Another, slower activity decay was often observed after longer duration of heat stress. This bimodal activity decay has been seen before, 51 and has been linked to structural collapse of the freeze-dried cake. The values of $\tau_{deact}$ quoted herein are all for the faster initial decay.

The initial value for each curve plotted in FIG. 1 gives an indication of the recovery of enzyme after the freeze-drying step only. The fraction of enzyme survival after only freeze-drying was not quantitatively measured (i.e. controls were not run from fresh enzyme solution on each plate), but a qualitative statement can be made from data about enzyme survival after freeze-drying. Those formulations described below that gave the best temporal stabilization in the glass also yielded the best enzyme recovery after freeze-drying.

Accelerated Testing

Several underlying physical processes may be involved in protein deactivation. Some of the possible factors include denaturation, deamination, or oxidation of key peptides, etc. Each of these processes will have an activation energy associated with it, and the overall deactivation process will have an apparent activation energy ($E_a$) which is some function of the individual activation energies. When the underlying physical processes (and thus the activation energies) that govern enzyme deactivation do not change perceptibly with temperature over a given temperature range, one expects that the characteristic deactivation time, $\tau_{deact}$, will be related to the absolute temperature by the following relationship:

$$\tau_{deact} \propto e^{-E_a/RT} \quad (1)$$

where the apparent activation energy, Ea is temperature independent. When this relationship holds, $\log(\tau_{deact})$ plotted against 1/T will be a straight line.

Figure 2:
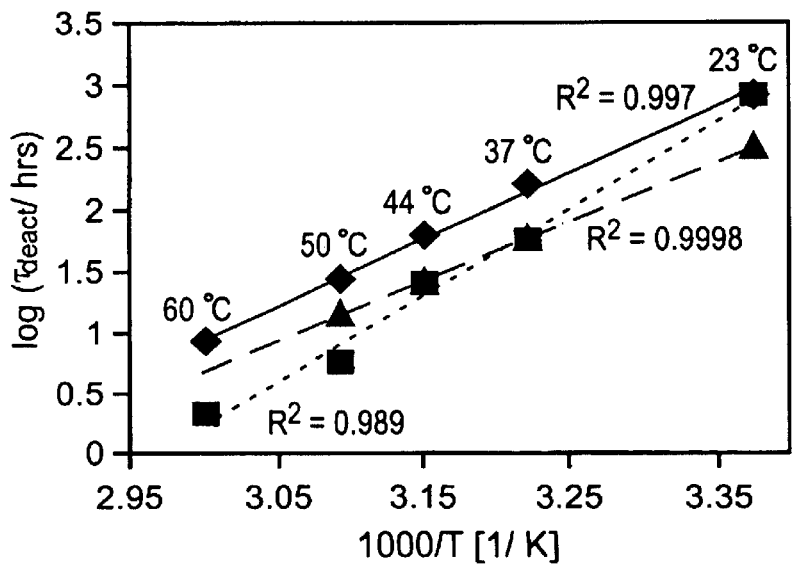
FIG. 2 shows enzyme deactivation times plotted in Arrhenius format.

FIG. 2 shows that the relationship expressed in equation (1) holds quite well for HRP in several protective glasses wherein we have measured $\tau_{deact}$ in the entire temperature range between 60° C. and 23° C. The same level of adherence to this relationship was observed for the one ADH formulation evaluated over the entire temperature range, namely ADH in trehalose. Enzyme deactivation in all formulations discussed herein follows the relationship suggested in equation (1) over the temperature range measured, with some possible exceptions, which will be noted below.

Approximately Arrhenius behavior is expected from measurements and calculations of glassy relaxation.[52] Arrhenius dynamics has previously been seen over this same temperature range for lifetime of protein deactivation[53,54] in lyophilized glassy formulations. Deviations from Arrhenius behavior was observed for formulations above their glass transition temperature,[55] but all formulations tested were well within the glassy regime at all testing temperatures. The observed constancy of this relationship herein provides the present inventors with the ability to reliably predict the efficacy of a particular formulation at room temperature by measuring its efficacy at several higher temperatures, and extrapolating.

This report contains data that clearly show excellent enzyme stability in some glasses at room temperature (i.e. the room temperature measurements have been made). Due to the length of time involved, it is impractical to measure the performance of all the formulations at room temperature. In most cases, reliance was placed on the extrapolations made from data in the range 60° C.–37° C. In view of the above discussion, these extrapolations provide, in almost all cases, a reasonably good estimate of the enzyme deactivation times. In the few cases where one might expect the linear extrapolation to be a poor estimate, the extrapolated values are believed to be an underestimation of $\tau_{deact}$, as will be discussed later. In all Figures herein, unfilled data points represent extrapolated data, whereas filled data points represent actual data. Bold entries in tables represent data that has been taken at room temperature as well as at the higher temperatures.

Results

A variety of small-molecule plasticizers were added to a variety of glass-forming, enzyme-stabilizing preparations. The formulations to which the plasticizers were added were organized into three basic groups: 1) small-molecule sugars and sugar alcohols (referred to as "non-polymeric" molecules); 2) polymeric sugars and synthetic polymers (referred to as "polymers"); 3) mixtures of polymers and linker molecules. (See below for definition of linker in this context.)

Plasticized Non-polymeric Glasses

Non-polymeric "standard materials," such as trehalose, lactose, raffinose, maltitol, etc. have been used as glassformers for preserving proteins in the dry state. Glasses made of these materials alone give reasonable service as preserving agents. However, it has been discovered that the addition of an appropriate plasticizer in the right proportion yields a new glass that has an increased enzyme-preserving efficacy.

FIG. 3 gives an example of a single-component trehalose glass that is improved by addition of a plasticizer, either DMSO or glycerol. Solid symbols represent lifetimes that were directly measured, whereas hollow symbols represent values that have been extrapolated. Two primary features were exhibited by these plasticized glasses. The first feature is that the apparent activation energy for HRP deactivation is much larger for the plasticized glass, as shown by the steeper slopes of the dashed lines in FIG. 3. The second feature is that deactivation times are much shorter for the plasticized glasses at elevated temperatures than they are for trehalose. The ADH data show these same features. The latter is probably related to the lower $T_g$ of the plasticized glasses.

FIG. 3 shows that when DMSO is added to a trehalose formulation so that the dried product contains 10 wt % DMSO, HRP is afforded protection against deactivation that is extrapolated to be 30 times better than the trehalose-only formulation at room temperature. There are at least two possible contributions to this improved stability. One possible contribution would be very general, and would come from modification of the properties of the glass itself. Another possible contribution to improved stability in the dry state could be due to specific interactions of the plasticizer with the protein.[56] Evidence suggests that there are contributions to increased stabilization due to both modification of the glass, and specific interactions. The data suggest that the relative importance of these contributions will vary from glass to glass. First, a 22-fold improvement in stabilization of ADH at room temperature in a 10 wt % DMSO-in-trehalose glass was observed compared to a trehalose-only glass. (See table 2 below.) This is slightly smaller than the 30-fold increase for the same glass with HRP. The present inventors are unaware of any specific interactions between DMSO and ADH, but know that DMSO interacts specifically with HRP.[57,58] This suggests that the majority (~95%) of the enhancement is due to modification of the properties of the glass in this case. On the other hand, a 5 wt % glycerol-in-trehalose glass preserves HRP 5 times longer than trehalose only, whereas a similarly plasticized glass gives a 30-fold increase in stabilization of ADH. ADH is a dehydrogenase for primary alcohols, and glycerol is known to modify its equilibrium conformation slightly at $pH \geq 8.0$.[59] If specific interactions are responsible for the additional increase in stability of ADH in the glycerol-plasticized glass, then such interactions probably account for approximately half of the stabilizing effect of ADH in glycerol/trehalose.

The results plotted in FIG. 3 show that increased protein stabilization can result from adding plasticizer to a bioprotective glass. However, as discussed above in the Statement of Related Art, the addition of too much plasticizer results in a glass that is not substantially more effective, or is even less effective than the unplasticized glass. In FIG. 4, values of HRP deactivation times evaluated at or extrapolated to room temperature are plotted against the mass fraction of DMSO in the dried product. It is seen that that there is a narrow concentration range over which DMSO has a beneficial effect for HRP in a trehalose glass. This somewhat striking feature has been verified by repeating the concentration study for HRP, but there is no ready explanation for it at this time. A very similar enhancement of ADH stability in 10 wt % DMSO/trehalose glass has been observed but DMSO concentration study for this enzyme has not been attempted. A much broader range of enhanced stabilization is seen for a DMSO-plasticized maltitol glass, although the maximum effect seems to be at about 10 wt %, as with the trehalose glass.

Figure 5:
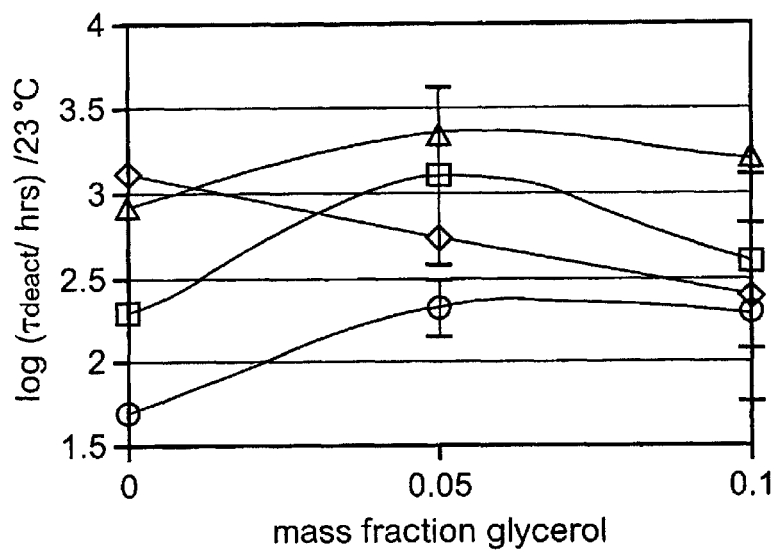
FIG. 5 shows HRP deactivation times extrapolated to room temperature for bioprotective glasses plasticized with varying amounts of glycerol.

FIG. 5 shows HRP deactivation times, evaluated at, or extrapolated to, room temperature for several glasses plasticized with varying amounts of glycerol. Similar to FIG. 4, the abscissa here is the amount of glycerol in the dried product. The main effect is similar to the general results shown in FIG. 4. Results of experiments on ADH in the trehalose/glycerol glasses listed in Table 2 below are consistent with the behavior of HRP in the trehalose/glycerol glasses plotted here. Raffinose is unusual among the sugars, sugar alcohols, and polymeric sugars that have examined because no beneficial effect was conferred by plasticization. It is possible that there is a beneficial effect at some concentration between 0 wt % and 5 wt % glycerol. Raffinose is a trisaccharide (the only one studied herein), but it is not clear if this has any bearing on the result.

Table 2 lists examples of single-component glasses made of non-polymeric standard materials, and some of their plasticized derivatives. The deactivation times in the unplasticized glass are listed. In all other cases (but one), only those formulations that showed improvement over the unplasticized glass were listed. As is indicated by FIGS. 4 and 5, the formulations listed in Table 2 are not the only ones that give improved performance, but they represent the best of those tested in this class.

TABLE 2

Performance of non-polymeric, plasticized glasses in biopreservation.

| Enzyme | Primary Glass-Former | Plasticizer | Mass fraction plasticizer | Expected value of log ($\tau_{deact}$/hrs) for enzyme at 23° C. | Improvement factor (over unplasticized glass at 23° C.) |
|---|---|---|---|---|---|
| HRP | Trehalose | — | — | 2.9 ± 0.2 | 1 |
| HRP | Trehalose | Glycerol | .05 | 3.66 ± 0.5 | 5 |
| HRP | Trehalose | DMSO | .1 | 4.4 ± 0.5 | 30 |
| HRP | Maltitol | — | — | 1.7 ± 0.5 | .06 |
| HRP | Maltitol | Glycerol | .05 | 2.3 ± 0.3 | 4 |
| HRP | Maltitol | DMSO | .1 | 2.8 ± 0.5 | 12 |
| HRP | Lactose | — | — | 2.7 ± 0.1 | .63 |
| HRP | Lactose | Glycerol | .05 | 3.0 ± 0.5 | 2 |
| ADH | Trehalose | — | — | 3.5 ± 0.2 | 1 |
| ADH | Trehalose | Glycerol | .05 | 5.0 ± 0.25 | 30 |
| ADH | Trehalose | Glycerol | .1 | 3.1 | 0.4 |
| ADH | Trehalose | DMSO | .1 | 4.85 ± 0.25 | 22 |

Plasticized Polymeric Glasses

Figure 6:
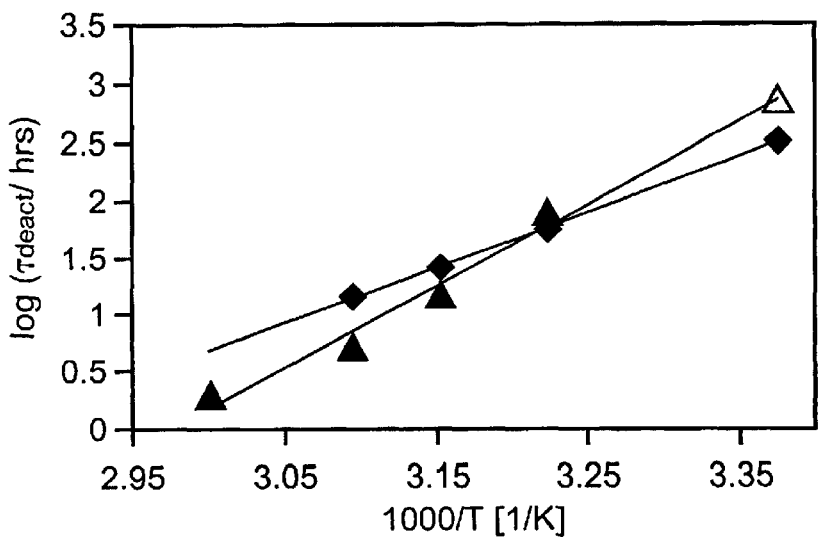
FIG. 6 shows temperature dependence of HRP deactivation time for dextran and 90% dextran, 10% glycerol.

FIG. 6 shows $\tau_{deact}$ for HRP in a dextran-only glass and in a dextran glycerol glass. HRP in a dextran-only glass is expected to have a value of $\tau_{deact}$ that is similar to that of HRP in a trehalose-only glass. However, the addition of a small amount of glycerol to a dextran glass gives a new glass with a twofold decrease in the lifetime for enzyme activity decay. It is of note that very different results were seen with ficoll (both 70 k and 400 k MW); addition of 10 wt % glycerol to ficoll produces a glass with a forty five-fold increase in the ability to preserve HRP against deactivation compared to ficoll only.

Although ficoll benefits greatly from the addition of glycerol as a plasticizer, dextran does not. The latter can be understood, at least in part, on the basis of dynamics of the plasticizer. In the absence of reasonably strong interactions, a guest-host system of primarily polymeric glassformer and a small amount of a small-molecule glassformer will exhibit bimodal dynamics wherein the small molecule guest is dynamically decoupled from the polymeric host glass[49]. In such a case, the plasticizer experiences a glass transition only at a temperature much lower than that required to induce a glass transition in the polymeric host, although the sample may appear glassy at the higher temperature.

It is believed that the full benefit of the plasticizer is not realized in these cases because the dynamics on the shorter lengthscale (lengthscale of the plasticizer) are much faster than dynamics characteristic of the glassy host. Accordingly, one of several "linker" molecules was incorporated in plasticized polymeric glasses with the intent of better coupling the dynamics of the polymeric glass and the small-molecule plasticizer.

Plasticized Polymeric Glasses with Linker Molecule

In order to realize the full benefit of the plasticizer in a polymeric glass, the plasticizer is dynamically coupled to the polymeric glassformer by means of a linker molecule. The linker may act in one or more of at least two potential ways. It may link the dynamics of the plasticizer with the polymeric host through attractive interactions with the plasticizer and/or host glassformer, or simply by virtue of its intermediate size and thus, its intermediate dynamics.

Polymeric and Oligomeric Linkers

Figure 7:
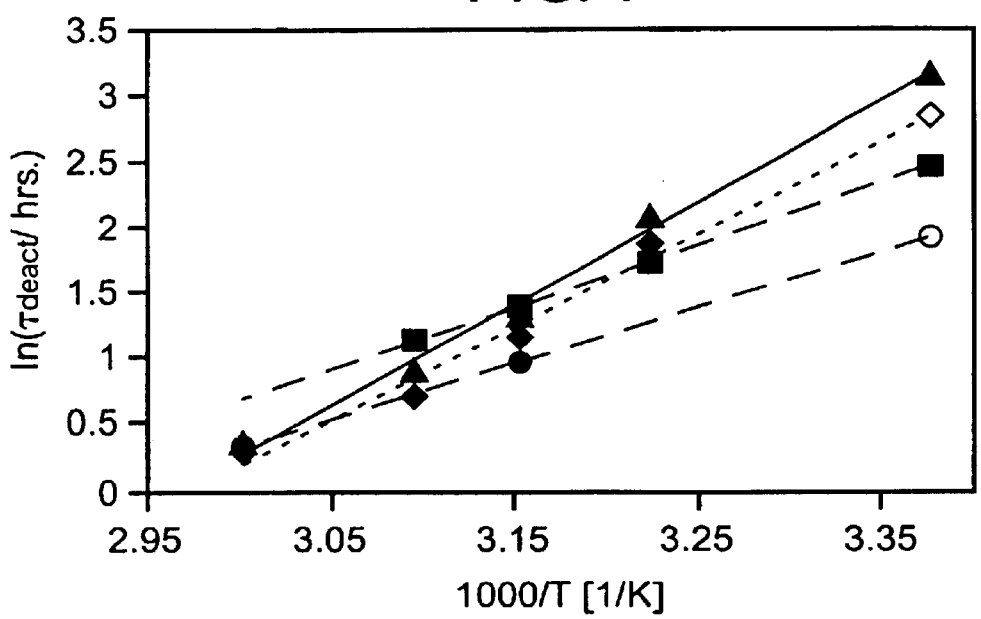
FIG. 7 shows protective properties of plasticized polymeric glasses.

A bioprotective glass made of dextran, inulin, and glycerol is significantly more effective at preserving HRP at room temperature than one made of any one or two of the components without the other(s). FIG. 7 shows the temperature dependence of $\tau_{deact}$ for HRP in bioprotective glasses made of dextran, of dextran with 10 wt % glycerol, of dextran with 10 wt % inulin, and of dextran with both inulin and glycerol at 10 wt % each. The glass with glycerol as plasticizer and inulin as a linker shows a twofold, fivefold, and seventeenfold improvement, respectively, in expected HRP stabilization at 23° C. over the glass with dextran only, dextran/glycerol only, or with dextran/inulin only. HRP in this new glass (dextran/inulin/glycerol) has a $\tau_{deact}$ value that is slightly better than trehalose at room temperature, and, by extrapolation, will exceed that of trehalose at lower temperatures. This can be seen more clearly in FIG. 2. Based on advertised prices,[60] the materials costs for a dextran/inulin/glycerol glass are a little over 10% that of an equal mass of trehalose.

It is believed that inulin acts as a dynamic linker in the dextran/inulin/glycerol glass discussed above. It may interact with glycerol via a non-specific interaction, such as a hydrophobic-type interaction, based on the following observations: Inulin is a polyfructose that is soluble in water only to about 4 wt %, approximately tenfold less water-soluble than are dextran or ficoll. Inulin is very soluble in glycerol (in excess of 50 wt %), and addition of glycerol to an aqueous solution significantly increases the solubility of inulin. A 50 wt % mixture of inulin and glycerol can form a gel in water. As the inulin and glycerol seem to interact to an appreciable extent, the inulin would be able to serve as a dynamic linker of the glycerol to the dextran by interacting also with the dextran by similar non-specific interactions, or simply by virtue of its size (or both).

Figure 8B:
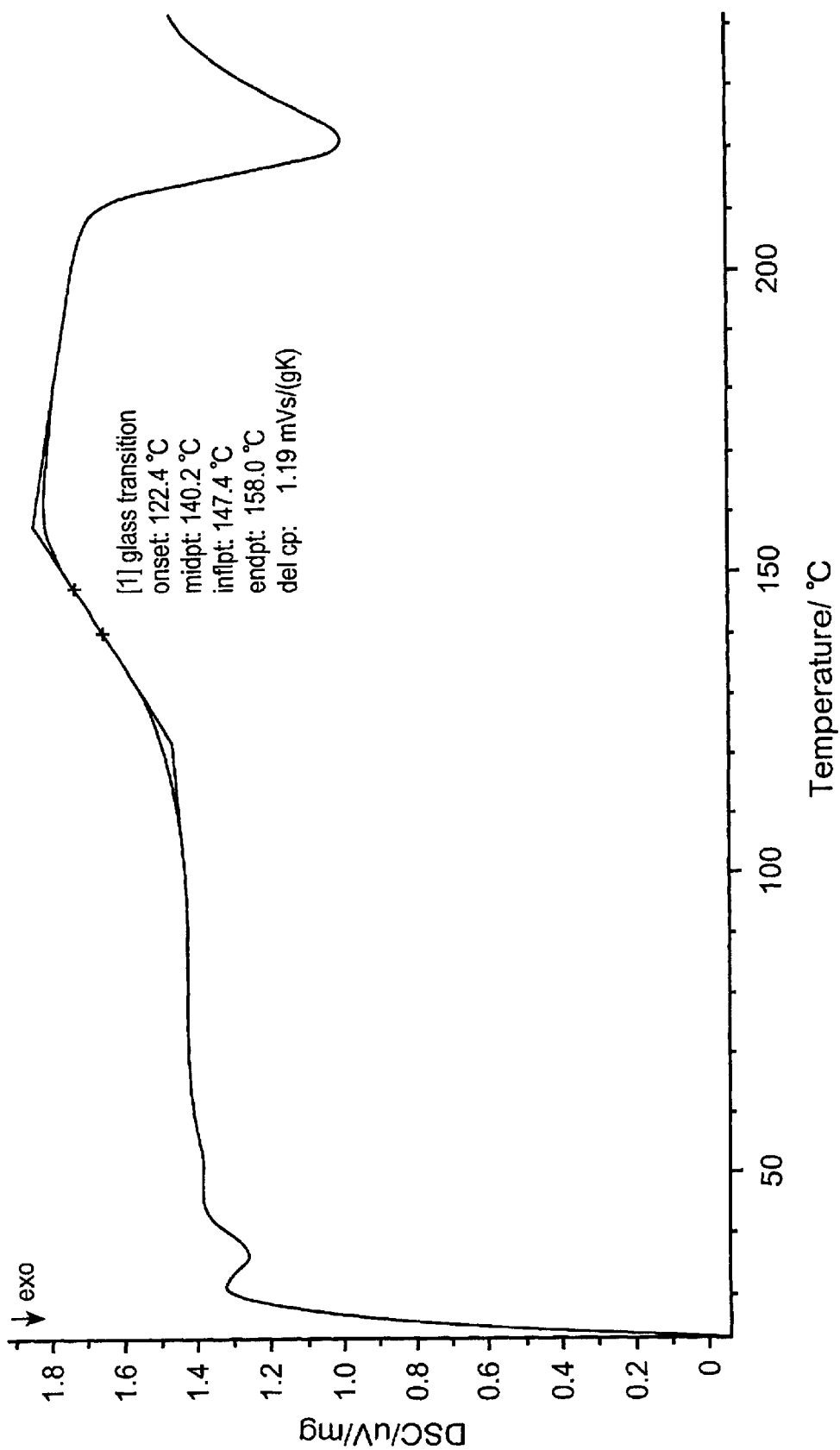
FIG. 8(b) shows a thermogram of 10% glycerol in dextran glass.

There is evidence that inulin does in fact act as a linker between the dynamics of the glycerol and the dextran. This evidence is found in differences seen in thermograms obtained from differential scanning calorimetry (DSC) of a series of glasses composed of dextran, inulin, and glycerol, and their mixtures. The glass transition of the dextran glass is shown in FIG. 8a, and has an onset of 218° C. and a width of 8° C. A mixture of 10 wt % glycerol in dextran, shown in FIG. 8b, has a transition onset of 122° C. and a width of about 35° C. The addition of only 10 wt % glycerol reduces $T_g$ by 96° C., and produces a fourfold increase in the width of the transition. The broad transition is consistent with a broad distribution of uncoupled dynamics expected for a polymer host and small-molecule guest with only weak interactions.

Figure 8C:
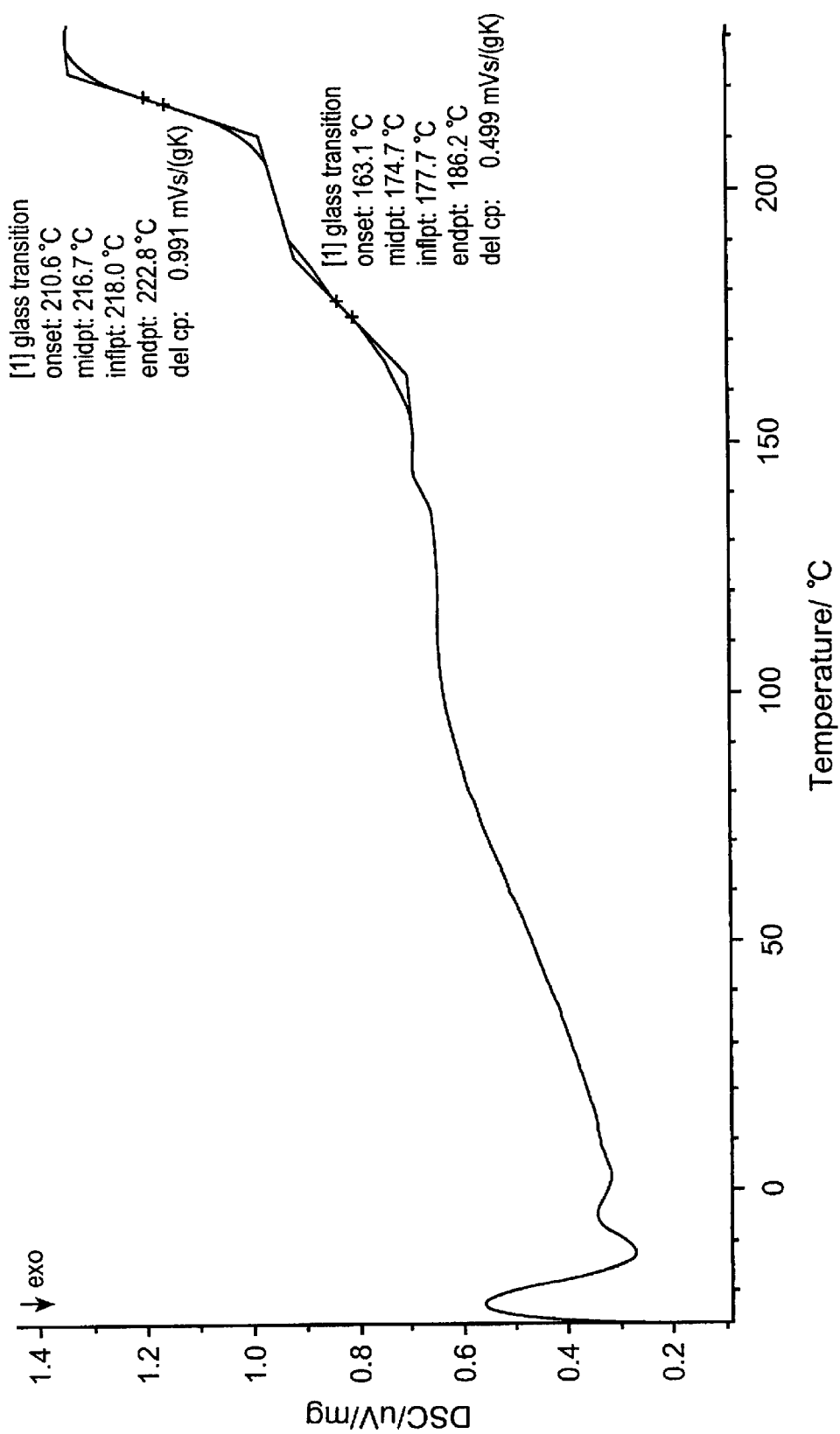
FIG. 8(c) shows a thermogram of 10% inulin in dextran glass.
Figure 8D:
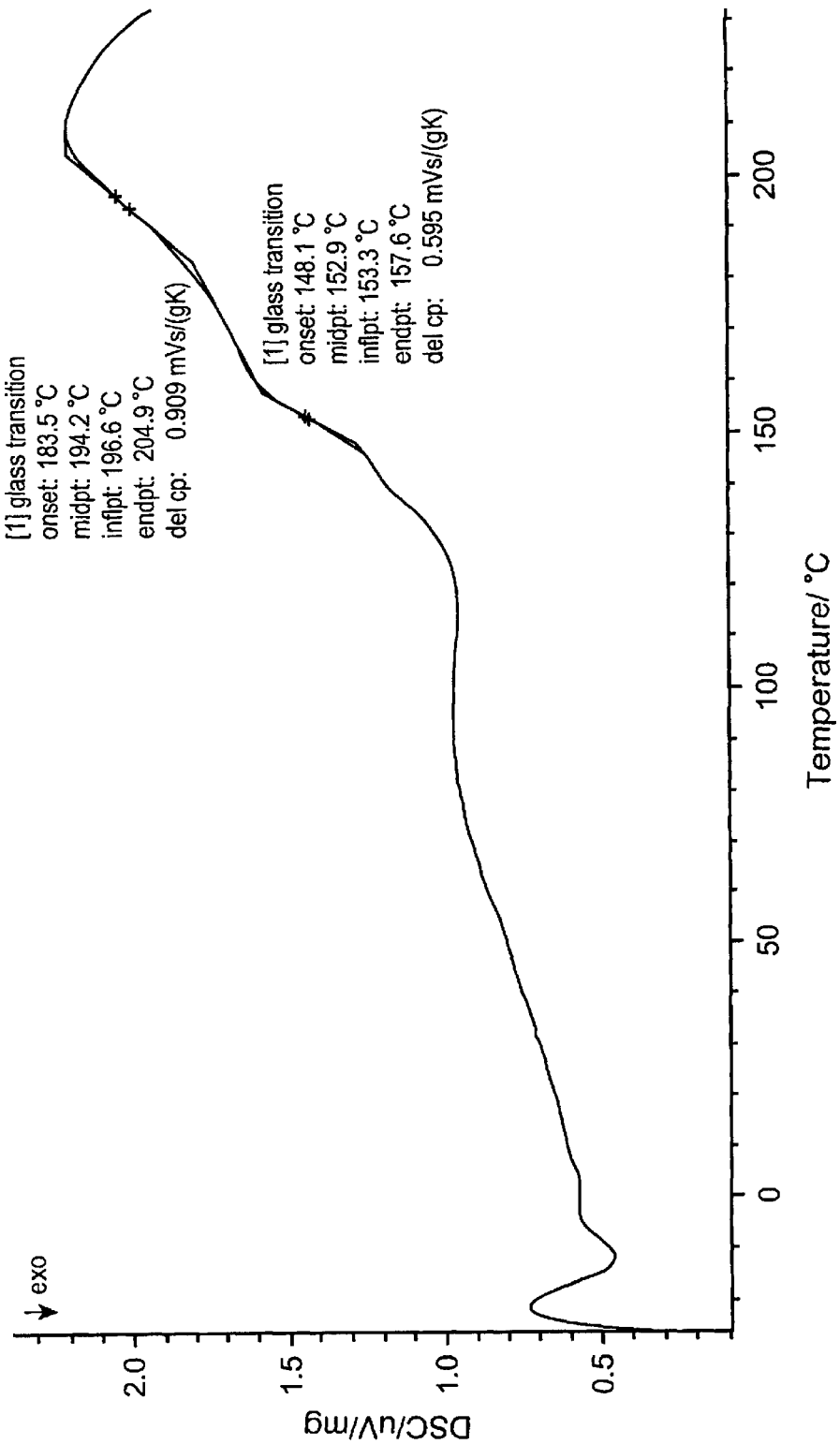
FIG. 8(d) shows a thermogram of 10% glycerol in dextran/inulin mixture.

FIG. 8c is a thermogram of a glass made of 10 wt % inulin in dextran. The two major transitions observed have onsets at 163° C. and 210' C; approximately 10° C. lower than the transition onset temperatures for pure inulin and pure dextran respectively,[61] with transition widths similar to that of dextran. FIG. 8d shows that when 10 wt % glycerol is added to a dextran/inulin mixture such as that of FIG. 8c, a minor plasticization occurs (~15° C.) and there is no detectable broadening of the transitions. This is evidence that the dynamics of the glycerol and the dynamics of the polymeric sugars are linked. Whatever the mode of coupling, it seems evident that the dynamics of the dextran/inulin/glycerol system are fairly well coupled. Furthermore, the room temperature value of $\tau_{deact}$ for HRP is markedly increased in dextran/inulin/glycerol system as compared to a dextran/glycerol system.

Other oligomers or polymers that are only slightly water-soluble are likely to act as couplers in a similar manner to inulin. A poly-proplyeneoxide (PPO) at two molecular weights (725 and 4000) has been tested as a dynamic linker by substituting these for inulin as a linker in a dextran/glycerol glass. The data listed in Table 3 shows that PPO is equally as effective in this role as is inulin.

The dextran/inulin system has been employed to investigate the effect of using plasticizers other than glycerol. Ethylene glycol, propylene glycol, and DMSO were all equally as effective as glycerol in this system. The results are listed in Table 3. The data in table 3 shows that this effect is not limited to dextran. Ficoll (70 k and 400 k showed identical results), PVP, and PVA all formed greatly improved bioprotective glasses in the presence of 10 wt % inulin and 10 wt % glycerol. The amounts of ingredient in these ternary systems have not been optimized, and the results listed here should be viewed as merely illustrative limits to the potential performance.

TABLE 3

Performance of polymeric glasses, plasticized and with polymeric dynamic linkers.

| Primary polymer | Linker/ mass fraction | Plasticizer/mass fraction | Expected value of Log($\tau_{deact}$/hrs) for HRP at 23° C. |
|---|---|---|---|
| Dextran | — | — | 2.86 ± 0.19 |
| Dextran | — | Glycerol/0.10 | 2.5 ± 0.08 |
| Dextran | Inulin/0.10 | Glycerol/0.10 | 3.2 ± 0.2 |
| Dextran | Inulin/0.10 | Ethylene Glycol/0.10 | 2.9 ± 0.2 |
| Dextran | Inulin/0.10 | Propylene Glycol/0.10 | 2.8 ± 0.2 |
| Dextran | Inulin/0.10 | DMSO/0.10 | 3.0 ± 0.2 |
| Dextran | PPO (725 MW)/0.10 | Glycerol/0.10 | 2.9 ± 0.4 |
| Dextran | PPO (4000 MW)/0.10 | Glycerol/0.10 | 2.9 ± 0.3 |
| Ficoll | — | — | 1.5 ± 0.1 |
| Ficoll | — | Glycerol/0.10 | 3.2 ± 0.3 |
| Ficoll | Inulin/0.10 | Glycerol/0.10 | 3.4 – 5.8* |
| PVP | — | — | 1.4 ± 0.5 |
| PVP | Inulin/0.10 | Glycerol/0.10 | 2.9 ± 0.5 |
| PVA | — | — | ~0 (no activity observed after freeze-drying) |
| PVA | Inulin/0.10 | Glycerol/0.10 | 3.0 ± 0.5 |

*This system appears to exhibit non-Arrhenius dynamics. The lower value assumes Arrhenius dynamics, the upper value is based on a quadratic fit to four data points. See FIG. 10 and accompanying text.

Non-polymeric Linkers

Previously, it was shown that linker molecules with molecular weights of about 725 and greater could be effective in coupling the dynamics of the polymeric glassformer and the plasticizer. Here we see that sugars and sugar alcohols can serve the same purpose. Plasticized polymeric glasses have been prepared with intermediate-sized, non-polymeric linker molecules. A significant increase was observed in the values of $\tau_{deact}$ for HRP when these linker compounds are added to the plasticized polymeric glass. FIG. 9 gives an example of improved biopreservation in such a dynamically linked, plasticized system. FIG. 9 shows $\tau_{deact}$ values for HRP in dextran/glycerol glasses with and without a non-polymeric linker. The small-molecule linker (maltitol in this case) gives a similar effect to that of inulin, but of greater amplitude. The expected room-temperature value Of $\tau_{deact}$ for the dextran/maltitol/glycerol system is $10^{3.6}$ hours, which is a threefold increase over the values we obtain for a dextran/inulin/glycerol glass.

One can achieve the type of dynamic coupling seen in DSC data that was provided by inulin in the dextran/inulin/glycerol systems, but with a nonpolymeric linker. This is borne out by DSC results similar to those shown in FIG. 8. Two glass transitions are seen in a 10 wt % lactose in dextran glass, with onset temperatures at 205° C. and 163° C., and widths of 10° C. and 25° C. respectively. The addition of 10 wt % glycerol to this glass reduces both the glass transitions by 40° C., but does not change the width of the transitions at all. As before, the absence of a significantly broadened transition suggests that the plasticizer is more-or-less dynamically linked to the polymer.

Table 4 summarizes the results for some of the systems tested. Entries have been included for unplasticized glasses and plasticized, but "dynamically unlinked" glasses as reference glasses for the dextran and ficoll systems in with HRP. In some other cases, and for all of the ADH-stabilizing glasses, there were no such reference glasses with which to compare, so $\tau_{deact}$ 23° C. for the enzyme in trehalose was used as a benchmark. The last column of Table 4 gives the ratio of $\tau_{deact}$ at 23° C. of the enzyme in the glass for that entry to $\tau_{deact}$ at 23° C. of the enzyme in trehalose. Several of the ternary mixtures below show great promise, giving projected values of $\tau_{deact}$ for HRP in the range of 3 to 200 times longer than those for trehalose at room temperature. As before, these formulations have not been optimized, and the results should be viewed as lower limits to the potential of these types of formulations.

the order of $3 \times \tau_{deact}$ to complete, and $10^{5.8}$ hours (projected $\tau_{deact}$ value for the ficoll/inulin/glycerol system at room temperature) is about 70 years.

SUMMARY

A novel approach has been described for preserving proteins in glass. The glasses tested herein are hydrophilic glass-forming materials commonly used for these purposes, but with a significant additive: a hydrophilic, small-molecule plasticizer, such as glycerol or DMSO is added which remarkably increases the bioprotective ability of the glasses. The data herein show that the bioprotective ability of plasticized polymeric glasses benefit from the addition of a linker molecule, which appears to couple together the dynamics of the plasticizer and the polymeric material. DSC data has been presented that supports the concept that these linkers do indeed act to "couple" the dynamics of the plasticizer and the bulk material.

By utilizing this approach, the present invention produces bioprotective glasses that perform hundreds of times better than unplasticized glass, and nearly one hundred times better than trehalose at room temperature, and with materials that

TABLE 4

Performance of polymeric glasses, plasticized and with non-polymeric dynamic linkers.

| Enzyme | Primary polymer | Linker/mass fraction | Plasticizer/mass fraction | Expected value of log($\tau_{deact}$/hrs) for enzyme at 23° C. | Improvement factor (over trehalose at 23° C.) |
|---|---|---|---|---|---|
| HRP | Dextran | — | — | 2.86 ± 0.19 | 1 |
| HRP | Dextran | — | Glycerol/0.10 | 2.5 ± 0.08 | .4 |
| HRP | Dextran | Maltitol/0.15 | Glycerol/0.15 | 3.6 ± .35 | 5 |
| HRP | Dextran | Maltitol/0.10 | Ethylene Glycol/0.10 | 3.5 – 5.2* | 4–200* |
| HRP | Dextran | Maltitol/0.10 | Propylene Glycol/0.10 | 1.5 ± .3 | .1 |
| HRP | Dextran | Maltitol/0.10 | DMSO/0.10 | 4.8 ± 0.5 | 80 |
| HRP | Dextran | Sorbitol/0.15 | Glycerol/0.15 | 3.4 ± 0.16 | 3 |
| HRP | Dextran | Lactose/0.10 | Glycerol/0.10 | 3.2 ± .3 | 2 |
| HRP | Dextran | Raffinose/0.10 | Glycerol/0.10 | 2.1 ± .4 | .6 |
| HRP | Ficoll | — | — | 1.5 ± 0.1 | .04 |
| HRP | Ficoll | — | Glycerol/0.10 | 2.7 | .63 |
| HRP | Ficoll | Maltitol/0.10 | Glycerol/0.10 | 3.8 ± 0.06 | 8 |
| HRP | Ficoll | Maltitol/0.10 | DMSO/0.10 | 4.4 ± .06 | 32 |
| HRP | PVP | — | — | 1.4 ± 0.5 | .03 |
| HRP | PVP | Maltitol/0.10 | Glycerol/0.10 | 3.6 ± 0.6 | 5 |
| HRP | PVA | — | — | 0 | 0 |
| HRP | PVA | Maltitol/0.10 | Glycerol/0.10 | 2.7 ± 0.1 | 1 |
| ADH | Dextran | Trehalose/0.10 | Glycerol/0.10 | 3.5 ± 0.7 | 1 |
| ADH | Dextran | Trehalose/0.10 | DMSO/0.10 | 3.7 ± 0.1 | 1.6 |
| ADH | Dectran | Maltitol/0.10 | Glycerol/0.10 | 4.2 ± 0.7 | 5 |
| ADH | Dextran | Maltitol/0.10 | DMSO/0.10 | 3.9 ± 0.3 | 2.5 |

*This system appears to exhibit non-Arrhenius dynamics. The lower value assumes Arrhenius dynamics, the upper value is based on a quadratic fit to four data points. See FIG. 10 and accompanying text.

Apparent Non-arrhenius Behavior

FIG. 10 displays data for two systems that show indications of non-Arrhenius behavior in their dynamics. The uncertainty in the $\tau_{deact}$ data for the ficoll/inulin/glycerol system (squares) is approximately the size of the symbols; the enzyme is HRP. It is not clear at this time why these systems would be non-Arrhenius, but if in fact they are, they would be truly excellent glasses for biopreservation at room temperature.

With the methods used herein, data was obtained at temperatures no lower than about 30° C. for these glasses, as the experiments would be too lengthy. Experiments take on cost significantly less than trehalose. Furthermore, the approach presented here allows the optimization of a stabilizing formulation for a particular storage temperature: both the temperature dependence and absolute value of enzyme deactivation time are modified by plasticization.

We have discussed and shown data for preservation of proteins in glass; however, the concept of plasticizing glasses for improved stability may be applied to areas such as preservation of bacteria (for food processing), biopolymers other than proteins, such as DNA and RNA, gene delivery systems, as in the stability of polymer-plasmid complexes, polymeric sustained-delivery depots, liposomes, similar nanostructures for drug delivery, and many other systems wherein material to be stored is placed in a non-cryogenic glass in order to minimize unwanted chemical and physical reactions, the rate of such being linked to the dynamics of the glassy host.

While the invention has been described with preferred embodiments, it is to be understood that variations and modifications may be resorted to as will be apparent to those skilled in the art. Such variations and modifications are to be considered within the purview and the scope of the claims appended hereto.

References

The following publications and patents are cited in this application as superscript numbers, 1–59.

[1] R. Mouradian, C. Womerseley, L. M. Crowe, and J. H. Crowe, Biochem. Biophys. Acta, 778 615 (1984).
[2] J. F. Carpenter, L. M. Crowe, and J. H. Crowe, Biochimica et Biophysica Acta 923, 109 (1987).
[3] Pikal, M. J., Rigsbee, D. R., The stability of insulin in crystalline and amorphous solids: observation of greater stability for the amorphous form. Pharm. Res. 14(10), 1379–1387 (1997).
[4] Izutsu, K.-I., Yoshioka, S., Terao, T., Effect of mannitol crystallinity on the stabilization of enzymes during freeze-drying. Pharm. Soc. Jap. 424(1), 5–8 (1994).
[5] Tanaka, K, Takeda, T., Miyajima, K., Cryoprotective effect of saccharides on denaturation of catalase by freeze-drying, Chem. Pharm. Bull. 39(5), 1091–1094 (1991).
[6] Constantino, H. R., Carrasquillo, K. G., Cordero, R. A., Mutenthaler, M., Hsu, C. C., Griebenwo, K, Effect of excipients on the stability and structure of lyophilized recombinant human growth hormone, J. Pharm. Sci, 87,1412–1420 (1998).
[7] Cleland J L, Lam X, Kendrick B, Yang J, Yang T H, Overcashier D, Brooks D, Hsu C,Carpenter J F, A specific molar ratio of stabilizer to protein is required for storage stability of a lyophilized monoclonal antibody. J Pharm Sci 90(3):310–21 (2001).
[8] Carpenter, J. F., Crowe, L. M., and Crowe J. H., Stabilization of phosphofructokinase with sugars during freeze-drying: characterization of enhanced protection in the presence of divalent cations, Biochim. Biophys. Acta. 923, 109–115 (1987).
[9] J. F. Carpenter, B. Martin, L. M. Crowe, and J. H. Crowe, Cryobiology 24, 445 (1987).
[10] Mazzobre M F, Del Pilar Buera M., Combined effects of trehalose and cations on the thermal resistance of beta-galactosidase in freeze-dried systems. Biochim Biophys Acta 1473(2–3):337–44 (1999).
[11] Chang B S, Kendrick B S, Carpenter J F., Surface-induced denaturation of proteins during freezing and its inhibition by surfactants. J Pharm Sci 85(12): 1325–30 (1996)
[12] J. F. Carpenter, B. Martin, S H. Loomis, and J. H. Crowe, Cryobiology 25, 327 (1988).
[13] Franks, et al., U.S. Pat. No. 6,071,428 Jun. 6, 2000.
[14] Magneson, et al. U.S. Pat. No. 5,547,873 Aug. 20, 1996
[15] Roser U.S. Pat. No. 5,149,653 Sep. 22, 1992
[16] Hinrichs W L, Prinsen M G, Frijlink H W, Inulin glasses for the stabilization of therapeutic proteins. Hinrichs W L, Prinsen M G, Frijlink H W.Int J Pharm 215(1–2):163–74 (2001).
[17] Sun, W. Q. and P. Davidson, Effect of dextran molecular weight on protein stabilization during freeze-drying and storage, CryoLett. 22, 258–292 (2001).
[18] Anchordoquy T J, Izutsu K I, Randolph T W, Carpenter J F, Maintenance of quaternary structure in the frozen state stabilizes lactate dehydrogenase during freeze-drying. Arch. Biochem. Biophys. 390(1), 35–41 (2001).
[19] Walker, et al. U.S. Pat. No. 5,565,318 Oct. 15, 1996
[20] Yoshioka S, Aso Y, Kojima S, Tanimoto T., Effect of polymer excipients on the enzyme activity of lyophilized bilirubin oxidase and beta-galactosidase formulations. Chem Pharm Bull (Tokyo) 48(2):283–5 (2000).
[21] Mattern M, Winter G, Kohnert U, Lee G., Formulation of proteins in vacuum-dried glasses. II. Process and storage stability in sugar-free amino acid systems. Pharm Dev Technol 4(2):199–208 (1999).
[22] Saleeb, et al U.S. Pat. No. 5,972,395; Oct. 26, 1999.
[23] Allison S D, Manning M C, Randolph T W, Middleton K, Davis A, Carpenter J F., Optimization of storage stability of lyophilized actin using combinations of disaccharides and dextran. J Pharm Sci 89(2): 199–214 (2000).
[24] Kreilgaard L, Frokjaer S, Flink J M, Randolph T W, Carpenter J F. Effects of additives on the stability of recombinant human factor XIII during freeze-drying and storage in the dried solid. Arch Biochem Biophys 360(1):121–34 (1998).
[25] Izutsu K, Yoshioka S, Kojima S., Increased stabilizing effects of amphiphilic excipients on freeze-drying of lactate dehydrogenase (LDH) by dispersion into sugar matrices. Pharm Res 12(6):838–43 (1995).
[26] Kim A l, Akers M J, Nail S L. The physical state of mannitol after freeze-drying: effects of mannitol concentration, freezing rate, and a noncrystallizing cosolute. J Pharm Sci 87(8):931–5 (1998).
[27] Lueckel B, Bodmer D, Helk B, Leuenberger H., Formulations of sugars with amino acids or mannitol-influence of concentration ratio on the properties of the freeze-concentrate and the lyophilizate. Pharm Dev Technol 3(3):325–36 (1998).
[28] Kasraian K, Spitznagel T M, Juneau J A, Ylm K., Characterization of the sucrose/glycine/water system by differential scanning calorimetry and freeze-drying microscopy. Pharm Dev Technol 3(2):233–9 (1998).
[29] Heller M C, Carpenter J F, Randolph T W., Protein formulation and lyophilization cycle design: prevention of damage due to freeze-concentration induced phase separation. Biotechnol Bioeng 63(2):166–74 (1999).
[30] Lueckel B, Helk B, Bodmer D, Leuenberger H. Effects of formulation and process variables on the aggregation of freeze-dried interleukin-6 (IL-6) after lyophilization and on storage. Pharm. Dev. Technol. 3(3):337–46 (1998).
[31] Conrad P B, Miller D P, Cielenski P R, de Pablo J J., Stabilization and preservation of *Lactobacillus acidophilus* in saccharide matrices. Cryobiology 41(1):17–24 2000.
[32] Miller, D. P., Andreson, R. E., and de Pablo, J. J., Stabilization of lactate dehydrogenase following freeze-thawing and vacuum-drying in the presence of trehalose and borate, Pharm. Res. 15 (8), 1215–1221 (1998).
[33] Her, L. M., Deras, M., Nail, S. M., Electrolyte-induced changes in glass transition temperatures of freeze-concentrated solutes, Pharm. Res. 12 (5), 768–772 (1995).
[34] Miller, D. P, de Pablo, J. J., Corti, H. R, Viscosity and glass transition temperature of aqueous mixtures of trehalose with borax and sodium chloride, J. Phys. Chem. B. 103, 10243–10249 (1999).
[35] Kasralan K, DeLuca P P. The effect of tertiary butyl alcohol on the resistance of the dry product layer during primary drying. Pharm Res 12(4):491–5 (1995).
[36] Carpenter, J. F., Pikal, M. J., Chang, B. S., Randolph, T. W., Rational design of stable lyophilized protein formulations: some practical advice. Pharm. Res. 14(8), 969–975 (1997).
[37] Bell, L. N., Haeman, M. J., and Muraoka, L. M., Thermally induced denaturation of lyophilized bovine somatotropin and lysozyme as impacted by moisture and excipients, J. Pharm. Sci., 84 (6), 707–712 (1995).

[38]Buitink, J., Dries, 1. J. van den, Hoekstra, F. A, Alberda, M., and Hemminga, M. A., High Critical Temperature above $T_g$ May Contribute to the Stability of Biological Systems, Biophys. J. 79(2), 1119–1128 (2000).

[39]S. P. Dudu, and P. R. Dal Monte, Pharm. Research, 14, 591 (1997).

[40]Wang, W., Lyophilization and development of solid protein pharmaceuticals, Int. J. Pharm. 203, 1–60 (2000).

[41]Tan, C. S., van Ingen, C. W., Talsma, H., van Miltenburg, J. C., Setffensen, C. L., Vlug, Ij. A., and Stalpers, J. A., Freeze-drying of fungi: influence of composition and glass transition temperature of the protectant, Cryobiology 32, 60–67 (1995).

[42]Uritani, M., Tanai, M., Yoshinaga, K, Protective effect of disaccharides on restriction endonuclease during drying under vacuum. J. Bioichem 117, 774–779 (1995).

[43]Buera, M. P., Rossi, S., Moreno, S., Chirife, J., Stabilization of restriction enzyme EcoRi dried with trehalose and other selected glass-forming solutes, Biotechnol. Prog. 13, 609–616 (1997).

[44]Rariy, R. V., Klibanov, A. M., Correct protein folding in glycerol, Proc. Natl. Acad. Sci, USA 94, 13520–13523 (1997).

[45]Carpenter, J. F., Crowe, J. H, Modes of stabilization of a protein by organic solutes during desiccation, Cryobiology 25, 459–470 (1988).

[46]Buera, M. P., Rossi, S., Moreno, S., Chirife, J., DSC confirmation that vitrification is not necessary for stabilization of the restriction enzyme ecoRI dried with saccharides, Biotechnol. Prog. 15, 577–579 (1999)

[47]Gekko, K., Timasheff, S. N., Mechanism of protein stabilization by glycerol: preferential hydration in glycerol-water mixtures, Biochemistry 20, 4667–4676 (1981).

[48]T. Inoue, M. T. Cicerone, and M. D. Ediger, Macromolecules 28, 3425 (1995).

[49]M. Vogel, P. Medick, E. Rossler, J. Mol. Liquids 86, 103 (2000)

[50]K. C. Fox, Putting proteins under glass. Science 267, 1992 (1995).

[51]Sun, W. Q. and Davidson, P., Effect of dextran molecular weight on protein stabilization during freeze-drying and storage, CryoLetters 22, 258–292 (2001).

[52]Shamblin, S. L., Tang, X., Chang, L., Hancock, B. C., and Pikal, M. J., Characterization of the time scales of molecular motion in pharmaceutically important glasses. J. Phys. Chem. B 103, 4113–4121 (1999).

[53]Mazzobre, M. F., Buera, M. P., Chirife, H., Glass transition and thermal stability of lactase in low-moisture amorphous polymeric matrices. Biotechnol. Prog. 13, 195–199 (1997).

[54]Yoshioka, S., Aso, Y., Izutsu, K.-I., Terao, T., Application of accelerated testing for shelf-life prediction of commercial protein preparations. J. Pharm. Sci. 83, 454–456 (1994).

[55]Sun, W. Q., Davidson, P., Chan, H. S. O., Protein stability in the amorphous carbohydrate matrix: relevance to anhydrobiosis. Biochim. Biophys. Acta. 1425, 245–254 (1998).

[56]Encinas, M V, Gonzalez-Nilo F D, Andreu J M, Alfonso C, Cardemil E. urea-induced unfolding studies of free- an ligand-bound tetrameric ATP-dependent saccharomyces cerevisiae phosphoenolupyruvate carbohykinase. Influence of quaternary structure on protein conformational stability. Int. J. Biochem. Cell Biol. 34(6): 645–56 (2002).

[57]Gebicka, L., and Gabicki, J. L., Dimethyl sulfoxide rather than superoxide is the reactive species in horseradish peroxidase-$KO_2$/dimethyl sufloxide system, Biochem. Mol. Bio. Int. 37(5) 1021–1026 (1995).

[58]Duran, N., Baeza, J., Freer, F., Brunet, J. E., Gonzalez, F. A., Sotomayor, C. P., Faljoni-Alario, A., Dimethyl sulfoxide as a chemical and biological probe: conformational effect on peroxidase systems, Biochem. And Biophys. Res. Comm. 103(1), 131–138 (1981).

[59]Myers, J. S., Jakoby, W. B., Glycerol as an agent eliciting small conformational changes in alcohol dehydrogenase. J. Biol. Chem. 250 (10), 3785–3789 (1975).

[60]1999 Prices from Sigma for small (not bulk) quantities.

[61]The reduction in Tg for both of these peaks may be due to the fact that the mixtures for which data is shown here all contained 0.4 wt % surfactant, whereas the thermograms from single component materials (dextran and inulin) were from samples with no surfactant added.

All of the above publications and patents are herein incorporated by reference in their entirety to the same extent as if each individual publication or patent was specifically and individually indicated to be incorporated by reference in its entirety.

What is claimed is:

1. A storage-stable composition comprising:
   (a) at least one biological agent;
   (b) from about 3% to about 15% by weight of the composition of at least one non-crystallizing, plasticizing agent; and
   (c) a glassy matrix.

2. The composition according to claim 1, wherein the biological agent comprises a protein.

3. The composition according to claim 2, wherein the protein comprises at least one enzyme.

4. The composition according to claim 1, wherein the plasticizing agent comprises glycerol or a glycol.

5. The composition according to claim 1, wherein the plasticizing agent comprises dimethyl sulfoxide.

6. The composition according to claim 1, wherein the plasticizing agent interacts with the biological agent so as to modify its equilibrium structure and/or stabilize it.

7. The composition according to claim 4, wherein the glycol comprises ethylene or propylene glycol.

8. The composition according to claim 1, wherein the glassy matrix comprises a carbohydrate, a synthetic polymer, a polyscaccharide or a sugar alcohol.

9. The composition according to claim 8, wherein the carbohydrate comprises a sugar.

10. The composition according to claim 8, wherein the synthetic polymer comprises diethylaminoethyldextran, dextran sulfate, polyethylene glycol, polyvinyl pyrrolidone, polyacrylamide or polyethyleneimine.

11. The composition according to claim 1, wherein the glassy matrix comprises an amino acid.

12. The composition according to claim 1, wherein the plasticizing agent is present in an amount of 5 to 10% by weight of the composition.

13. A solid storage-stable composition comprising:
   (a) at least one biological agent;
   (b) from about 3% to about 30% by weight of the composition of at least one non-crystallizing, small-molecule, plasticizing agent;
   (c) at least one linking compound; and
   (d) at least one glassy matrix.

14. The composition of claim 13, wherein the biological agent comprises a protein.

15. The composition of claim 14, wherein the protein comprises an enzyme.

16. The composition of claim 13, wherein the plasticizing agent comprises glycerol, a glycol or dimethyl sulfoxide.

17. The composition of claim 13, wherein the plasticizing agent is present in an amount of 5 to 20 weight % based on the total weight of the composition.

18. The composition of claim 13, wherein the glassy matrix comprises at least one sugar alcohol, carbohydrate, polysaccharide, amino acid or synthetic polymer.

19. The composition of claim 13, wherein the linking compound comprises inulin or polypropylene oxide.

20. A method for preparing the composition of claim 1 which comprises the steps of:
   (a) preparing an aqueous solution or dispersion comprising a bioactive material, a plasticizing compound and a glass precursor;
   (b) drying the aqueous dispersion; and
   (c) recovering a composition wherein the bioactive material is dispersed in a glassy matrix containing the plasticizing compound.

21. The method of claim 20, wherein the drying step is effected by freeze-drying.

22. The method of claim 20, further comprising at least one linking compound.

23. A storage-stable composition comprising:
   (a) at least one biological agent;
   (b) at least one non-crystallizing, plasticizing agent present in the composition in an amount sufficient to improve the stability of the biological agent upon lyophilization in comparison to the stability of a lyophilized composition containing said biological agent alone in a glassy matrix, the maximum amount of plasticizing agent being that concentration at which the composition is no longer in a glassy state at the storage temperature of the composition; and
   (c) a glassy matrix.

24. The composition of claim 23, wherein the biological agent is a protein or an enzyme.

25. The composition of claim 24, wherein the plasticizing agent is selected from the group consisting of ethylene glycol, glycerol, propylene glycol and dimethyl sulfoxide.

26. The composition of claim 24, wherein the glassy matrix is selected from the group consisting of a carbohydrate, a synthetic polymer, a polysaccharide and a sugar alcohol.

* * * * *